(12) United States Patent
Ye et al.

(10) Patent No.: US 12,158,409 B2
(45) Date of Patent: Dec. 3, 2024

(54) BLOOD ANALYSIS SYSTEM, BLOOD ANALYZER, BLOOD ANALYSIS METHOD AND STORAGE MEDIUM

(71) Applicant: Shenzhen Mindray Bio-Medical Electronics Co., Ltd., Shenzhen (CN)

(72) Inventors: Bo Ye, Shenzhen (CN); Huan Qi, Shenzhen (CN); Wenbo Zheng, Shenzhen (CN); Yi Ye, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 875 days.

(21) Appl. No.: 17/079,158

(22) Filed: Oct. 23, 2020

(65) Prior Publication Data

US 2021/0041344 A1 Feb. 11, 2021

Related U.S. Application Data

(63) Continuation of application No. PCT/CN2019/084685, filed on Apr. 26, 2019.

(30) Foreign Application Priority Data

Apr. 28, 2018 (WO) ................ PCT/CN2018/085199

(51) Int. Cl.
*G01N 15/1429* (2024.01)
*G01N 33/49* (2006.01)

(52) U.S. Cl.
CPC ..... *G01N 15/1429* (2013.01); *G01N 33/4915* (2013.01)

(58) Field of Classification Search
CPC .......... G01N 15/1429; G01N 15/1459; G01N 2015/0084; G01N 2015/1402; G01N 33/4915
See application file for complete search history.

(56) References Cited

U.S. PATENT DOCUMENTS

| | | | |
|---|---|---|---|
| 2001/0052763 A1 | 12/2001 | North, Jr. | |
| 2003/0102220 A1* | 6/2003 | Nagai | G01N 15/1209 204/600 |

(Continued)

FOREIGN PATENT DOCUMENTS

| | | |
|---|---|---|
| CN | 103471982 A | 12/2013 |
| CN | 103837502 A | 6/2014 |

(Continued)

OTHER PUBLICATIONS

China National Intellectual Property Administration, Chinese Application No. 201980008250.0, Office Action dated Oct. 24, 2022, 11 pages.

*Primary Examiner* — Jennifer Wecker
(74) *Attorney, Agent, or Firm* — Kory D. Christensen

(57) ABSTRACT

Disclosed are a blood analysis system, a blood analyzer, a blood analysis method and a storage medium. The blood analysis method includes: acquiring at least two types of optical signals of a test sample derived from a blood sample, wherein red blood cells in the test sample are lysed, blood cells in the test sample are stained by a fluorescence dye, and the at least two types of optical signals include scattered light signals and/or fluorescent signals; generating a scattergram based on the at least two types of optical signals; identifying a preset region in the scattergram based on the at least two types of optical signals; and acquiring detection data of a platelet subpopulation based on the preset region.

17 Claims, 14 Drawing Sheets

(56) References Cited

U.S. PATENT DOCUMENTS

| | | | |
|---|---|---|---|
| 2005/0002826 A1* | 1/2005 | Oguni | G01N 33/5094 |
| | | | 436/63 |
| 2005/0079623 A1* | 4/2005 | Ortiz | G01N 15/1459 |
| | | | 436/63 |
| 2007/0218558 A1* | 9/2007 | Ortiz | G01N 33/96 |
| | | | 436/63 |
| 2007/0231913 A1 | 10/2007 | Tsuji et al. | |
| 2009/0312955 A1 | 12/2009 | Hutchins et al. | |
| 2010/0248247 A1* | 9/2010 | Kataoka | G01N 15/1429 |
| | | | 435/6.1 |
| 2011/0077870 A1* | 3/2011 | Linssen | G01N 15/147 |
| | | | 702/19 |
| 2014/0147837 A1 | 5/2014 | Kimura et al. | |
| 2017/0074863 A1* | 3/2017 | Masuda | G01N 15/1429 |
| 2018/0003634 A1* | 1/2018 | Bo | G01N 33/49 |
| 2020/0158615 A1* | 5/2020 | Shi | G01N 15/1459 |

FOREIGN PATENT DOCUMENTS

| | | | |
|---|---|---|---|
| CN | 103852404 A | 6/2014 | |
| CN | 104075976 A | 10/2014 | |
| CN | 104297135 A | 1/2015 | |
| CN | 104297213 A | 1/2015 | |
| CN | 104541149 A | 4/2015 | |
| CN | 105372216 A | 3/2016 | |
| CN | 105467109 A2 | 4/2016 | |
| CN | 105973811 A | 9/2016 | |
| CN | 106525666 A | 3/2017 | |
| CN | 106662572 A | 5/2017 | |
| CN | 106687810 A | 5/2017 | |
| JP | 2016186463 A | 10/2016 | |
| WO | 2015030184 A1 | 3/2015 | |
| WO | WO-2018231835 A1 * | 12/2018 | G01N 15/0205 |

* cited by examiner

//blood analysis system, blood analyzer, blood analysis method and storage medium

CROSS-REFERENCE

This application is a continuation of International Application No. PCT/CN2019/084685, filed Apr. 26, 2019, which claims priority benefit of International Application No. PCT/CN2018/085199, filed Apr. 28, 2018, the contents of which are incorporated herein by reference.

TECHNICAL FIELD

The present disclosure relates to the field of in vitro detection, and in particular, to a blood analyzer, a blood analysis system, an analysis method of a blood sample and a storage medium thereof.

BACKGROUND ART

Blood analysis is widely used in medical research and detection to acquire related information about blood cells including red blood cells, white blood cells, platelets, etc. Commonly used automated blood analyzers generally analyze blood cells in blood samples based on the electrical impedance principle (also known as Coulter Principle). According to the electrical impedance principle, when particles suspended in an electrolyte pass through a detection aperture with the electrolyte, the equivalent resistance across the detection aperture will change. Under effect of a constant current source cross the detection aperture, the voltage across the detection aperture will change. The changes in the voltage across the detection aperture are collected by a circuit system, and voltage pulse waveforms can thus be generated, wherein amplitudes of the pulse waveforms reflect volume sizes of the particles. The analyzers can provide information about volume distribution of particles in samples according to the acquired pulse waveforms. For blood samples, the blood analyzers can provide a volume distribution histogram of blood cells in a test blood sample based on the electrical impedance principle, and then acquire blood analysis data such as cell classification, cell count and the like by analyzing the volume distribution histogram.

However, detection signals based on the electrical impedance principle can only reflect information about volume of particles passing through the detection aperture, and cannot be used to differentiate among different particles with a same or similar volume. For example, blood cell analysis methods based on the electrical impedance method cannot be used to differentiate among large platelets, red blood cell fragments (schistocytes) and microcytes with a similar volume, and the blood analyzers may mistakenly count a large platelet with relatively large volume as a red blood cell, resulting in false decrease in large platelet detection results, and the blood analyzers may also mistakenly count a red blood cell with relatively small volume (such as a red blood cell fragment and a microcyte) as a large platelet, resulting in false increase in large platelet detection results. Moreover, except for mature platelets and large platelets, platelets also include immature platelets, and counting of immature platelets is of great importance to analyze platelet production kinetics and mechanism of thrombocytopenia. In prior art, platelets and their subpopulations (such as large platelets and immature platelets) can be differentiated from blood cells such as red blood cells and the like by specific staining, thereby acquiring an accurate detection result of platelets and their subpopulations. However, these methods require a separate detection channel and separate detection reagents, which increases cost of blood analyzers and cost of reagents in blood analysis process.

SUMMARY

An aspect of embodiments of the present disclosure includes an analysis method of a blood sample, wherein the method comprises: acquiring at least two types of optical signals of a test sample derived from a blood sample, wherein red blood cells in the test sample are lysed, and blood cells in the test sample are stained by a fluorescence dye, and the at least two types of optical signals comprise scattered light signals and/or fluorescent signals; generating a scattergram of the test sample based on the at least two types of optical signals; identifying a preset region in the scattergram based on the at least two types of optical signals; and acquiring detection data of a platelet subpopulation in the test sample based on the preset region.

Further, in the analysis method provided by embodiments of the present disclosure, generating a scattergram of the test sample based on the at least two types of optical signals comprises generating a scattergram of the test sample based on forward scattered light signals and fluorescent signals.

Further, the analysis method provided by embodiments of the present disclosure further comprises: classifying white blood cells in the test sample into white blood cell subpopulations based on the at least two types of optical signals of the test sample.

Further, the analysis method provided by embodiments of the present disclosure comprises: classifying white blood cells in the test sample into neutrophils, lymphocytes, monocytes and eosinophils, or classifying white blood cells in the test sample into basophils; or counting white blood cells in the test sample; or identifying nucleated red blood cells or immature white blood cells or blast cells in the test sample.

Further, in the analysis method provided by embodiments of the present disclosure, acquiring detection data of a platelet subpopulation in the test sample based on the preset region comprises: acquiring volume distribution data of the platelet subpopulation in the test sample based on forward scattered light signals of a particle population characterized in the preset region.

Further, in the analysis method provided by embodiments of the present disclosure, the at least two types of optical signals further comprise side scattered light signals; acquiring detection data of a platelet subpopulation in the test sample based on the preset region comprises: acquiring the volume distribution data of the platelet subpopulation in the test sample based on forward scattered light signals and side scattered light signals of the particle population characterized in the preset region.

Further, in the analysis method provided by embodiments of the present disclosure, generating a scattergram of the test sample based on the at least two types of optical signals comprises generating a scattergram of the test sample based on side scattered light signals and fluorescent signals.

Further, the analysis method provided by embodiments of the present disclosure further comprises: detecting forward scattered light signals of a particle population characterized in the preset region, classifying white blood cells in the test sample into neutrophils, lymphocytes, monocytes and eosinophils, or classifying white blood cells in the test sample into basophils; or detecting forward scattered light signals of a particle population characterized in the preset region, counting white blood cells in the test sample; or detecting forward scattered light signals of a particle population characterized in the preset region, and identifying nucleated red blood cells or immature white blood cells or blast cells in the test sample.

Further, in the analysis method provided by embodiments of the present disclosure, acquiring detection data of a platelet subpopulation in the test sample based on the preset region comprises: acquiring volume distribution data of the platelet subpopulation in the test sample based on forward scattered light signals of the particle population characterized in the preset region.

Further, in the analysis method provided by embodiments of the present disclosure, generating a scattergram of the test sample based on the two types of optical signals comprises generating a scattergram of the test sample based on forward scattered light signals and side scattered light signals.

Further, in the analysis method provided by embodiments of the present disclosure, acquiring detection data of a platelet subpopulation in the test sample based on the preset region comprises: acquiring volume distribution data of the platelet subpopulation in the test sample based on forward scattered light signals of a particle population characterized in the preset region.

Further, in the analysis method provided by embodiments of the present disclosure, the at least two types of optical signals further comprise fluorescent signals, and the method further includes: classifying white blood cells in the test sample into neutrophils, lymphocytes, monocytes and eosinophils, or classifying white blood cells in the test sample into basophils; or counting white blood cells in the test sample; or identifying nucleated red blood cells or immature white blood cells or blast cells in the test sample.

Further, the analysis method provided by embodiments of the present disclosure comprises: determining whether the detection data of the platelet subpopulation is abnormal; and providing an alarm, if the detection data of the platelet subpopulation is determined to be abnormal.

Further, the analysis method provided by embodiments of the present disclosure comprises: outputting at least one of: the detection data of platelets subpopulations, the preset region and the scatter diagram with the preset region being marked.

Further, the analysis method provided by embodiments of the present disclosure comprises: acquiring a platelet count of the blood sample; calculating a ratio of the platelet subpopulation based on the detection data of the platelet subpopulation and the platelet count.

Further, in the analysis method provided by embodiments of the present disclosure, the platelet subpopulation is large platelet subpopulation or immature platelet subpopulation.

An aspect of embodiments of the present disclosure provides a non-volatile computer-readable storage medium with a computer program stored thereon, wherein the computer program, when executed by a processor, implements steps of any analysis method aforementioned.

An aspect of embodiments of the present disclosure includes a blood analysis system, comprising: a sample treatment device comprising at least one mixing chamber which is configured to mix a first aliquot of a blood sample with a lytic reagent to prepare a first test sample, wherein the lytic reagent comprises a hemolytic agent for lysing red blood cells and a fluorescence dye for staining white blood cells; a sample detection device comprising an optical detection unit, wherein the optical detection unit comprises an optical flow chamber, a light source and an optical detector, wherein the optical flow chamber is in fluid communication with the mixing chamber, the light source is configured to direct a light beam to the optical flow chamber, the optical detector is configured to detect at least two types of optical signals of the first test sample passing through the optical flow chamber, and the at least two types of optical signals comprise forward scattered light signals and fluorescent signals; and a data analysis module comprising a signal acquisition module and a classification and counting module; wherein the signal acquisition module is configured to acquire the at least two types of optical signals of the first test sample; and the classification and counting module is configured to generate a scattergram of the first test sample based on the at least two types of optical signals, differentiate between a white blood cell region and a preset region, and acquire detection data of a platelet subpopulation in the first test sample based on the preset region.

Further, in the blood analysis system provided by embodiments of the present disclosure, the classification and counting module is configured to, when generating a scattergram of the first test sample based on the at least two types of optical signals, generate a scattergram of the first test sample based on forward scattered light signals and fluorescent signals.

Further, in the blood analysis system provided by embodiments of the present disclosure, the classification and counting module is configured to classify white blood cells in the first test sample into white blood cell subpopulations.

Further, in the blood analysis system provided by embodiments of the present disclosure, the classification and counting module is configured to classify white blood cells in the first test sample into neutrophils, lymphocytes, monocytes and eosinophils or classify white blood cells in the first test sample into basophils; or count white blood cells in the first test sample; or identify nucleated red blood cells or immature white blood cells or blast cells in the first test sample.

Further, in the blood analysis system provided by embodiments of the present disclosure, the classification and counting module is configured to acquire volume distribution data of the platelet subpopulation in the first test sample based on forward scattered light signals of a particle population characterized in the preset region.

Further, in the blood analysis system provided by embodiments of the present disclosure, the at least two types of optical signals detected by the optical detector further comprise side scattered light signals; and the classification and counting module is configured to acquire the volume distribution data of the platelet subpopulation in the first test sample based on forward scattered light signals and side scattered light signals of the particle population characterized in the preset region.

Further, in the blood analysis system provided by embodiments of the present disclosure, the classification and counting module is configured to, when generating a scattergram of the first test sample based on the at least two types of optical signals, generate a scattergram of the first test sample based on side scattered light signals and fluorescent signals.

Further, the blood analysis system provided by embodiments of the present disclosure, further comprising: the optical detector is further configured to detect forward scattered light signals of a particle population characterized in the preset region; the classification and counting module is configured to classify white blood cells in the first test sample into neutrophils, lymphocytes, monocytes and eosinophils or classify white blood cells in the first test sample into basophils; or count white blood cells in the first test sample; or identify nucleated red blood cells or immature white blood cells or blast cells in the first test sample.

Further, in the blood analysis system provided by embodiments of the present disclosure, the classification and counting module is configured to acquire volume distribution data of the platelet subpopulation in the first test sample based on forward scattered light signals of the particle population characterized in the preset region.

Further, in the blood analysis system provided by embodiments of the present disclosure, the classification and counting module is configured to, when generating a scattergram of the first test sample based on the two types of optical signals generate a scattergram of the first test sample based on forward scattered light signals and side scattered light signals.

Further, in the blood analysis system provided by embodiments of the present disclosure, the classification and counting module is configured to acquire volume distribution data of the platelet subpopulation in the first test sample based on forward scattered light signals of a particle population characterized in the preset region.

Further, in the blood analysis system provided by embodiments of the present disclosure, the at least two types of optical signals detected by the optical detector further comprise fluorescent signals; and the classification and counting module is configured to classify white blood cells in the first test sample into neutrophils, lymphocytes, monocytes and eosinophils or classify white blood cells in the first test sample into basophils; or count white blood cells in the first test sample; or identify nucleated red blood cells or immature white blood cells or blast cells in the first test sample.

Further, the blood analysis system provided by embodiments of the present disclosure further comprises an alarm module, wherein the alarm module is configured to determine whether the detection data of the platelet subpopulation is abnormal, and provide an alarm if the detection data of the platelet subpopulation is determined to be abnormal.

Further, the blood analysis system provided by embodiments of the present disclosure further comprises a user interface, wherein the data analysis module is configured to output at least one of the detection data of the platelet subpopulation, the preset region and the scattergram with the preset region being marked to the user interface.

Further, in the blood analysis system provided by embodiments of the present disclosure, the sample treatment device is further configured to mix a second aliquot of the blood sample with a diluent agent to prepare a second test sample; the sample detection device further comprises an electrical impedance detection unit, wherein the electrical impedance detection unit comprises an aperture and an electrical impedance detector, and the electrical impedance detector is configured to detect electrical impedance signals of the second test sample passing through the aperture; the signal acquisition module of the data analysis module is configured to acquire the electrical impedance signals of the second test sample; the classification and counting module is configured to acquire a platelet count of the second test sample based on the electrical impedance signals, and calculate a ratio of the platelet subpopulation based on the detection data of the platelet subpopulation and the platelet count.

Further, in the blood analysis system provided by the embodiments of the present disclosure, the platelet subpopulation is large platelet subpopulation or immature platelet subpopulation.

Another aspect of embodiments of the present disclosure provides an analysis method of a blood sample, comprising: acquiring at least two types of optical signals of a test sample derived from the blood sample, wherein red blood cells in the test sample are lysed, and the at least two types of optical signals comprise first scattered light signals and second scattered light signals, wherein the first scattered light signals are forward scattered light signals, and the second scattered light signal are at least one type of medium-angle scattered light signals and side scattered light signals; generating a scattergram of the test sample based on the at least two types of optical signals; differentiating between a white blood cell region and a large platelet region in the scattergram; and acquiring detection data of large platelets in the test sample based on the large platelet region.

Further, in the analysis method provided by embodiments of the present disclosure, acquiring detection data of large platelets in the test sample based on the large platelet region comprises: acquiring volume distribution data of large platelets in the test sample based on forward scattered light signals of a particle population characterized in the large platelet region.

Further, in the analysis method provided by embodiments of the present disclosure, the second scattered light signals are side scattered light signals; and acquiring detection data of large platelets in the test sample based on the large platelet region comprises: acquiring the volume distribution data of large platelets in the test sample based on forward scattered light signals and side scattered light signals of the particle population characterized in the large platelet region.

Further, in the analysis method provided by embodiments of the present disclosure, acquiring detection data of large platelets in the test sample based on the large platelet region includes: acquiring a number of particles in the large platelet region, and a count value of large platelets in the test sample based on the number of particles.

Further, the analysis method provided by embodiments of the present disclosure comprises: determining whether the detection data of large platelets is abnormal; providing an alarm, if the detection data of large platelets is determined to be abnormal.

Further, the analysis method provided by embodiments of the present disclosure comprises: outputting at least one of: the detection data of large platelets, the large platelet region and the scattergram with the large platelet region being marked.

Further, the analysis method provided by embodiments of the present disclosure comprises: acquiring a platelet count of the blood sample, and calculating a ratio of large platelets based on the detection data of large platelets and the platelet count.

Further, the analysis method provided by embodiments of the present disclosure comprises: classifying particle populations in the white blood cell region into white blood cell subpopulations.

Further, the analysis method provided by embodiments of the present disclosure further comprises: classifying white blood cells in the test sample into neutrophils, lymphocytes, monocytes and eosinophils, or classifying white blood cells in the test sample into basophils; or counting white blood cells in the test sample.

An aspect of embodiments of the present disclosure includes a non-volatile computer-readable storage medium with a computer program stored thereon, wherein the computer program, when executed by a processor, implements steps of any analysis method aforementioned.

Another aspect of embodiments of the present disclosure includes a blood analysis system, comprising: a sample treatment device comprising at least one mixing chamber which is configured to mix a first aliquot of a blood sample with a lytic reagent to prepare a first test sample, wherein the lytic reagent comprises a hemolytic agent for lysing red blood cells; a sample detection device comprising an optical detection unit, wherein the optical detection unit comprises an optical flow chamber, a light source and an optical detector, wherein the optical flow chamber is in fluid communication with the mixing chamber, the light source is configured to direct a light beam to the optical flow chamber, the optical detector is configured to detect at least two types of optical signals of the first test sample passing through the optical flow chamber, and the at least two types of optical signals comprise first scattered light signals and second scattered light signals, wherein the first scattered light signals are forward scattered light signal, and the second scattered light signals are at least one type of medium-angle scattered light signals and side scattered light signals; and a data analysis module comprising a signal acquisition module and a classification and counting module; wherein the signal acquisition module is configured to acquire the at least two types of optical signals of the first test sample; and the classification and counting module is configured to generate a scattergram of the first test sample based on the at least two types of optical signals, differentiate between a white blood cell region and a large platelet region in the scattergram, and acquire detection data of large platelets in the first test sample based on the large platelet region.

Further, in the blood analysis system provided by embodiments of the present disclosure, the classification and counting module is configured to acquire volume distribution data of large platelets in the first test sample based on forward scattered light signals of a particle population characterized in the large platelet region.

Further, in the blood analysis system provided by embodiments of the present disclosure, the second scattered light signals are side scattered light signals; and the classification and counting module is configured to acquire the volume distribution data of large platelets in the first test sample based on forward scattered light signals and side scattered light signals of the particle population characterized in the large platelet region.

Further, in the blood analysis system provided by embodiments of the present disclosure, the classification and counting module is configured to acquire a number of particles in the large platelet region, and obtain a count value of large platelets in the first test sample based on the number of particles.

Further, the blood analysis system provided by embodiments of the present disclosure further comprises an alarm module, wherein the alarm module is configured to determine whether the detection data of large platelets is abnormal, and provide an alarm if the detection data of large platelets is determined to be abnormal.

Further, the blood analysis system provided by embodiments of the present disclosure further comprises a user interface, wherein the data analysis module is configured to output at least one of the detection data of large platelets, the large platelet region and the scattergram with the large platelet region being marked to the user interface.

Further, in the blood analysis system provided by embodiments of the present disclosure, the sample treatment device is further configured to mix a second aliquot of the blood sample with a diluent agent to prepare a second test sample; the sample detection device further comprises an electrical impedance detection unit, wherein the electrical impedance detection unit comprises an aperture and an electrical impedance detector, and the electrical impedance detector is configured to detect electrical impedance signals of the second test sample passing through the aperture; the signal acquisition module of the data analysis module is configured to acquire the electrical impedance signals of the second test sample; and the classification and counting module is configured to acquire a platelet count of the second test sample based on the electrical impedance signals, and calculate a ratio of large platelets based on the detection data of large platelets and the platelet count.

Further, in the blood analysis system provided by embodiments of the present disclosure, the classification and counting module is configured to classify particle populations in the white blood cell region into white blood cell subpopulations.

Further, in the blood analysis system provided by embodiments of the present disclosure, the classification and counting module is configured to classify white blood cells in the first test sample into neutrophils, lymphocytes, monocytes and eosinophils or classify white blood cells in the first test sample into basophils; or count white blood cells in the first test sample.

With respect to the prior art, the blood analysis methods, systems, analyzers, and the storage mediums provided by the present disclosure provide users with information related to large platelets and/or immature platelets in blood samples, without significantly increasing costs of analyzers and reagents. The blood analysis methods, systems, analyzers, and the storage medium provided by the present disclosure can make use of optical detection signals from hemolytic channel for white blood cell detection in existing blood analyzers to obtain information related to large platelets and/or immature platelets. Moreover, the blood analysis systems and analyzers provided by the present disclosure have a lower cost compared with existing products with a function of detecting large platelets and/or immature platelets.

LIST OF REFERENCE NUMERALS

| Blood analysis system | 1, 2 |
| --- | --- |
| Sample collection unit | 10 |
| Sample treatment device | 20 |
| Mixing chamber | 210 |
| First mixing chamber | 221 |
| Second mixing chamber | 222 |
| Sample detection device | 50 |
| Optical detection unit | 53 |
| Optical flow chamber | 532 |
| Light source | 534 |
| Optical detector | 536 |
| Electrical impedance detection unit | 55 |
| Bus | 60 |
| Data analysis module | 70 |
| Storage system | 710 |
| Processor | 730 |
| Signal acquisition module | 750 |
| Classification and counting module | 770 |
| Alarm module | 790 |
| User interface | 90 |
| First housing | 100 |
| Second housing | 200 |

DETAILED DESCRIPTION OF EMBODIMENTS

The technical solution of the present disclosure will be described below with reference to the figures. It should be noted that when one unit is described as being "connected" to another unit, it may be directly connected to another unit or an intermediate unit may exist at the same time. When one unit is described as being "arranged" on another unit, it may be directly arranged on another unit or an intermediate unit may exist at the same time. Unless otherwise defined, all technical and scientific terms used herein have the same meaning as commonly understood by those skilled in the art. Names of elements or apparatuses used in the specification of the present disclosure are only intended to illustrate the specific embodiments instead of limiting the present disclosure.

A first aspect of the present disclosure relates to a blood analysis system, method, a blood analyzer and a storage medium for analyzing a platelet subpopulation in a blood sample. Specifically, the platelet subpopulation comprises large platelet subpopulation and immature platelet subpopulation.

Figure 1:
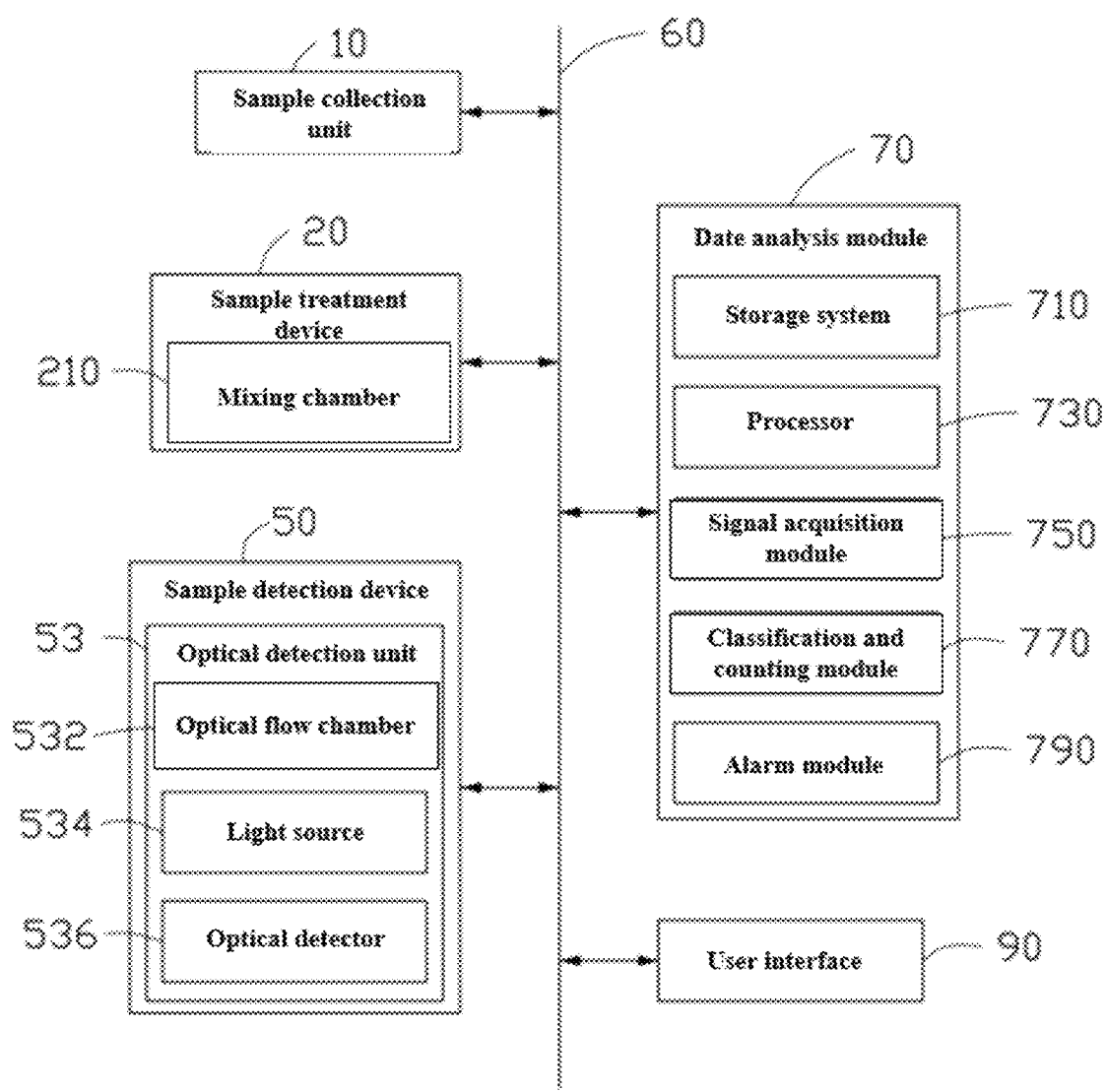
FIG. 1 is a schematic diagram of function modules of a blood analysis system provided by a first exemplary implementation of the present disclosure.

FIG. 1 is a schematic diagram of a blood analysis system. The blood analysis system 1 comprises a sample collection unit 10, a sample treatment device 20, a sample detection device 50, a data analysis module 70 and a user interface 90. The blood analysis system 1 is provided with a fluid flow system (not shown in the figure), which is configured to make the sample collection unit 10, the sample treatment device 20 and the sample detection device 50 in fluid communication for fluid transfer.

The sample collection unit 10 is configured to supply a blood sample to the sample treatment device 20. The sample treatment device 20 is configured to treat the blood sample for preparing a test sample and supply the test sample to the sample detection device 50. The sample treatment device 20 may comprise one or more mixing chambers for preparing the test blood sample into one or more test samples. The sample detection device 50 is configured to detect characteristics of particles in each test sample and acquire corresponding detection signals. The data analysis module 70 may be, directly or indirectly, connected electrically with the sample collection unit 10, the sample treatment device 20, the sample detection device 50 and the user interface 90 via a bus 60 to transmit and exchange data or signals.

In a first exemplary implementation of the present disclosure, the sample treatment device 20 comprises at least one mixing chamber 210, which is configured to mix the test blood sample with a lytic agent under certain reaction conditions to obtain a first test sample. The reaction conditions may be the same as or different from the hemolysis and/or staining conditions for classifying white blood cells in the prior art. Alternatively, the sample treatment device 20 may further comprise a sample dispenser, which is configured to dispense the test blood sample into several aliquots. Each aliquot of the blood sample is transferred to the same mixing chamber or different mixing chambers and then treated for subsequent detection. In the implementation, the lytic reagent comprises a hemolytic agent and a fluorescence dye. The hemolytic agent may be any one of existing hemolytic agents for classifying white blood cells by automated blood analyzers, wherein the hemolytic agent may be any one of a cationic surfactant, a nonionic surfactant, an anionic surfactant and an amphiphilic surfactant or any combination thereof. The fluorescence dye is used for staining blood cells. In some embodiments of the implementation, the fluorescence dye may be a nucleic acid dye, thereby classifying nucleated blood cells such as white blood cells, and other types of cells by measuring the differences in scattered light signals and fluorescent signals. In an embodiment of the implementation, the lytic reagent may be prepared by using the lytic reagent formula disclosed in U.S. Pat. No. 8,367,358, the entire disclosure of which is incorporated herein by reference. The lytic reagent disclosed in U.S. Pat. No. 8,367,358 comprises a cationic cyanine compound (a fluorescence dye), a cationic surfactant, a nonionic surfactant and an anionic compound. The lytic reagent may be used to lyse red blood cells and classify white blood cells into their subpopulations by detecting differences in scattered light intensities and fluorescence intensities. Other existing fluorescence dyes may also be used in the lytic reagent, for example, the fluorescence dye described in U.S. Pat. No. 8,273,329, the entire disclosure thereof is incorporated herein by reference. The lytic reagent containing such a fluorescence dye may be adopted to lyse red blood cells, identify and count nucleated red blood cells, white blood cells and the like, and further identify basophils in white blood cells by detecting differences in fluorescence intensities and forward scattered light intensities. Those skilled in the art may understand that the fluorescence dye may be contained in a separate staining solution, and such a staining solution can be used together with the hemolytic agent without a fluorescence dye. The staining solution may be added to the blood sample in the mixing chamber 210 before, after or upon the hemolytic agent is added for preparing the first test sample.

The sample detection device 50 at least comprises an optical detection unit 53. The optical detection unit 53 comprises a sheath flow system, an optical flow chamber 532, a light source 534, an optical detector 536 and a corresponding detection circuit. The optical flow chamber 532 is controllably in fluid communication with the mixing chamber 210, so that the first test sample is transferred by the sheath flow system from the mixing chamber 210 to the optical flow chamber 532. The light source 534 is configured to direct a light beam to the optical flow chamber 532. The optical detector 536 is configured to detect at least two types of optical signals of the first test sample. In the first exemplary implementation of the present disclosure, the at least two types of optical signals comprise forward scattered light signals and fluorescent signals, and the optical detector 536 of the optical detection unit 53 is set to be suitable for detecting forward scattered light signals and fluorescent signals of the first test sample passing through the optical flow chamber 532. In another embodiment, the at least two types of optical signals also comprise side scattered light signals, and the optical detector 536 is set to be suitable for detecting forward scattered light signals, side scattered light signals and fluorescent signals of the first test sample passing through the optical flow chamber 532.

Herein, the optical flow chamber refers to a focused-flow flow chamber suitable for detecting scattered signals and fluorescent signals, for example, the optical flow chambers used in existing flow cytometers and blood analyzers. When a particle, such as a blood cell, passes through an orifice of the optical flow chamber 532, the incident light beam emitted from the light source 534 and directed to the orifice is scattered by the particle in all directions. By arranging an optical detector at one or more angles with regard to the incident light beam, the light scattered by the particle can be detected to acquire scattered light signals. Since different blood cell populations have different light scattering properties, scattered light signals can be used to differentiate different cell populations. Specifically, scattered light signals detected near the incident light beam are generally referred to as forward scattered light signals or small-angle scattered light signals. In some embodiments, forward scattered light signals may be detected at an angle range from about 1° to about 10° with respect to the incident light beam. In some other embodiments, forward scattered light signals may be detected at an angle range from about 2° to about 6° with respect to the incident light beam. Scattered light signals detected at an angle of about 90° with respect to the incident light beam are generally referred to as side scattered light signals. In some embodiments, the side scattered light signals may be detected at an angle range from about 65° to about 115° with respect to the incident light beam. Generally, fluorescent signals emitted from blood cells stained by a fluorescence dye may be detected at an angle of about 90° with respect to the incident light beam.

The data analysis module 70 comprises a storage system 710 and a processor 730. The storage system 710 may store basic programs and data structures for implementing various functions of the methods disclosed herein. The storage system 710 may comprise one or more memories and one or more non-transitory computer-readable storage media. The non-transitory computer-readable storage media may include a Hard Disk Drive (HDD), a floppy disk, an optical disk, a Secure Digital Memory Card (SD Card), a flash memory card or the like. The memory may include a primary Random Access Memory (RAM) for storing program instructions and data or a Dynamic RAM (DRAM) and a Read Only Memory (ROM) for storing fixed instructions. The non-transitory computer-readable storage medium stores computer programs for implementing the methods disclosed by the present disclosure. The processor 730 comprises, but is not limited to, a Central Processing Unit (CPU), a Micro Controller Unit (MCU) and other devices for interpreting computer instructions and processing data in computer software. The processor 730 is configured to execute various computer programs in the non-transitory computer-readable storage medium, thereby enabling the blood analysis system 1 to execute the corresponding detection process, analyze and process the at least two types of optical signals detected by the sample detection device 50 in a real-time manner. In exemplary embodiments, the at least two types of optical signals may be processed by Field-Programmable Gate Array (FPGA), Digital Signal Processor (DSP) or CPU, and then automatically analyzed by the computer programs to acquire related data of platelets and/or platelet subpopulations.

In the first exemplary implementation, the data analysis module 70 further comprises a signal acquisition module 750 and a classification and counting module 770. The signal acquisition module 750 is operatively connected with one or more optical detectors 536 of the sample detection device 50 to acquire the forward scattered light signals and the fluorescent signals of the first test sample. The classification and counting module 770 is connected to the signal acquisition module 750. The classification and counting module 770 generates a scattergram of the first test sample based on the at least two types of optical signals, differentiates between a white blood cell region and a preset region in the scattergram, and acquires detection data of a platelet subpopulation of the first test sample based on the preset region in the scattergram. Scattergram or Histogram herein may be presented not only in a graphical form, but also in a data form, for example, a numeric form of a table or a list with the same or similar resolution as the scattergram or histogram, or may be presented in any other appropriate manner known in the art.

Classification and counting steps implemented when the processor executes the classification and counting module 770 will be further described below with reference to FIG. 2A, FIG. 2B and FIG. 3.

Figure 2A:
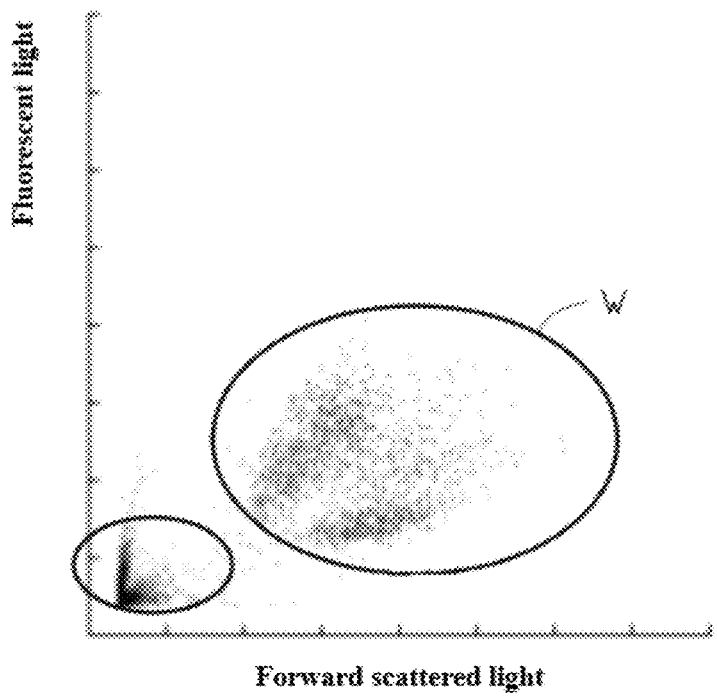
FIG. 2A is a fluorescent light-forward scattered light scattergram of a blood sample acquired by the first exemplary implementation of the present disclosure.
Figure 2B:
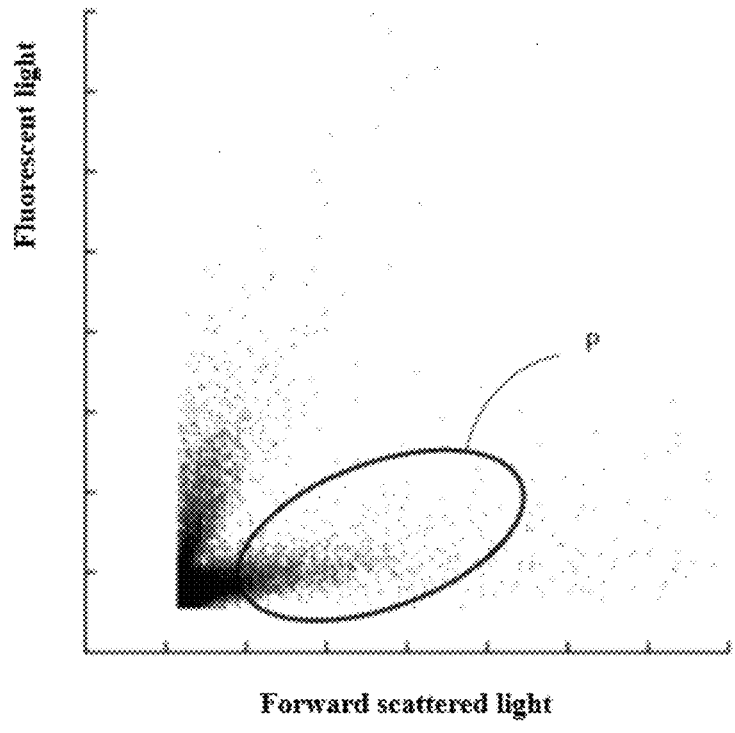
FIG. 2B is a partially enlarged view of FIG. 2A.

In the embodiment shown in FIG. 2A and FIG. 2B, a blood sample is treated and detected in the blood analysis system 1 provided by the first exemplary implementation, forward scattered light signals and fluorescent signals of the first test sample are acquired via the signal acquisition module 750, and then the classification and counting module 770 generates the scattergram of the first test sample shown in FIG. 2A based on the forward scattered light signals and the fluorescent signals. The scattergram may be a 2D scattergram with the intensities of the forward scattered light signals (FSC) of the first test sample as abscissa and the intensities of the fluorescent signals (FL) of the first test sample as ordinate. Those skilled in the art should understand that abscissa and ordinate of the scattergram are not limited to the presentation mode with linear coordinate axis and signal intensities shown in the embodiment, and abscissa and ordinate of the scattergram may also be other parameters of forward scattered light signals and fluorescent signals that reflect particle characteristics of the first test sample, and the abscissa and ordinate of the scattergram may also be nonlinear coordinate axis, such as logarithmic coordinate axis, to further highlight differences in distribution among particle populations.

The classification and counting module 770 differentiates between a white blood cell region W and a preset region P in the scattergram based on the differences in the intensities of the forward scattered light signals and the fluorescent signals of the first test sample, wherein the preset region P is a region where the platelet subpopulation (such as large platelets or immature platelets) appears in the scattergram. Those skilled in the art should understand that the white blood cell region W and the preset region P can be set by gating technique. As shown in FIG. 2A, it is generally well known to those skilled in the art that among particle populations characterized in the scattergram, the particle population with smallest forward scattered light signal intensities and smallest fluorescent signal intensities (located in the lower left corner of the scattergram) is mainly a population of red blood cell fragments. The inventor found after repeated assumptions and experiments that platelets treated by the hemolytic agent differ in volume size and cellular content from red blood cell fragments and white blood cells, and platelet subpopulations can be differentiated in the hemolyzed blood sample by an optical method. FIG. 2B is a partially enlarged view of FIG. 2A, wherein the region with relatively small abscissa values and ordinate values in the scattergram shown in FIG. 2A is enlarged. As shown in FIG. 2B, the intensities of the forward scattered light signals of the preset region P are substantially less than that of the white blood cell region W, and the intensities of the fluorescent signals of the preset region P are substantially less than that of the white blood cell region W. In the scattergram, the preset region P is basically located in the lower left of the white blood cell region W. Those skilled in the art should understand that the preset region P may be located at a fixed position in the scatter diagram, or determined according to the position of W.

The classification and counting module 770 may acquire detection data of a platelet subpopulation (such as large platelets or immature platelets) in the first test sample based on the preset region P in the scattergram. In an implementation, the classification and counting module 770 calculates volume distribution data of the platelet subpopulation in the test blood sample based on the forward scattered light signals of a particle population characterized in the preset region P. In an embodiment, the volume (Vol) of each particle in the preset region P may be calculated by using Equation (1):

$$\text{Vol}_a = \alpha * FSC \qquad \text{Equation (1)}$$

wherein, FSC is the intensity of forward scattered light signal of each particle (also referred to as "individual event") characterized in the preset region P, and $\alpha$ is a constant.

In another embodiment, the volume (Vol) of each particle in the preset region P may be calculated by using Equation (2):

$$\text{Vol}_b = \beta * \exp(\gamma * FSC) \qquad \text{Equation (2)}$$

wherein, FSC is the intensity of forward scattered light signal of each individual event characterized in the preset region P, and $\beta$ and $\gamma$ are constants.

In another embodiment, the volume (Vol) of each particle in the preset region P may be calculated using Equation (3):

$$\text{Vol}_c = [1/(FSC * \sigma(2\pi)^{1/2})] \exp(-\ln FSC - \mu)^2/2\sigma^2) \qquad \text{Equation (3)}$$

wherein, FSC is the intensity of forward scattered light signal of each individual event characterized in the preset region P, and $\mu$ and $\sigma$ are constants.

Figure 3:
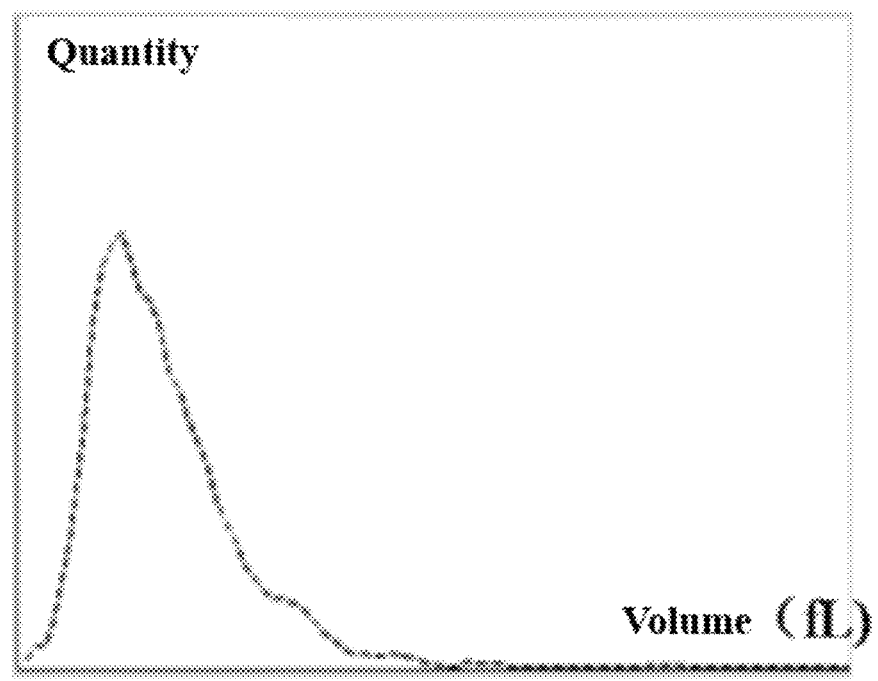
FIG. 3 is a volume distribution histogram of a platelet subpopulation in a blood sample acquired by the first exemplary implementation of the present disclosure.

The classification and counting module 770 may acquire a volume distribution curve (volume histogram) of the platelet subpopulation corresponding to the preset region P based on the volume (Vol) of each particle and the corresponding number of particles in the particle population characterized in the preset region P, as shown in FIG. 3. Thus, a volume distribution data of the platelet subpopulation in the blood sample may be acquired by the blood analysis system 1 provided by the first exemplary implementation of the present disclosure. The volume distribution data may be presented in a numerical form or a graphical form, such as a volume histogram. It can be understood that when the preset region P is a region where large platelets appear in the scattergram, volume distribution data of large platelets in the blood sample can be acquired by the blood analysis system 1 provided by the first exemplary implementation of the present disclosure; when the preset region P is a region where immature platelets appear in the scattergram, volume distribution data of immature platelets in the blood sample can be acquired by the blood analysis system 1 provided by the first exemplary implementation of the present disclosure.

Further, the classification and counting module 770 may further acquire a count of the platelet subpopulation and/or a count value of platelets within a specific volume range based on the volume distribution data of the platelet population. It can be understood that the function of counting the platelet subpopulation of the blood analysis system 1 provided by the first exemplary implementation is not limited to counting large platelets and/or immature platelets, and may further be counting a value of platelets with a volume larger than a preset volume threshold, wherein the volume threshold may be 10 fL, 12 fL, 15 fL, 20 fL or any other value between 10-20 fL. Moreover, the classification and counting module 770 may further acquire parameters reflecting distribution characteristic of the platelet subpopulation, such as volume distribution width of the platelet subpopulation, based on the volume distribution data of the platelet subpopulation, so that users of the blood analysis system 1 are provided with richer information about the test blood sample.

In another implementation, the classification and counting module 770 may acquire a number of particles (or referred to as "event number") in the preset region P, and acquire a count value of the platelet subpopulation in the blood sample based on the number of particles. It can be understood that when the preset region P is a region where large platelets appear in the scattergram, a count of large platelets in the blood sample can be acquired by the blood analysis system 1 provided by the first exemplary implementation of the present disclosure; when the preset region P is a region where immature platelets appear in the scattergram, a count of immature platelets in the blood sample can be acquired by the blood analysis system 1 provided by the first exemplary implementation of the present disclosure. Alternatively, the blood analysis system 1 may further obtain a count value of platelets within a specific volume range by changing the preset region P.

It should be noted that in the fluorescent light-forward scattered light (FL-FSC) scattergram generated and analyzed by the classification and counting module 770, there is a certain difference between the preset region P for classifying and counting large platelets and the preset region P' for classifying and counting immature platelets. Those skilled in the art should understand that forward scattered light signals are generally used to reflect volume information of blood cells, while fluorescent signals are generally used to reflect content information of blood cells. Large platelets are platelets having a relatively large volume. In clinical detection, sometimes platelets having a volume greater than 20 fL are identified as large platelets, and sometimes platelets having a volume greater than 12 fL are identified as large platelets. Based on the systems and methods provided by the present disclosure, a volume threshold for identifying large platelets can be set according to users' needs, that is, forward scattered light signals of the preset region P for differentiating large platelets should be greater than a certain preset threshold. Immature platelets are newly released platelets in blood circulation, and have relatively high RNA content compared with other types of platelets. Therefore, immature platelets in the first test sample of the present disclosure possess a relatively high fluorescent signal intensity, and fluorescent signals of the preset region P' for differentiating immature platelets should be greater than a certain preset threshold.

Figure 4A:
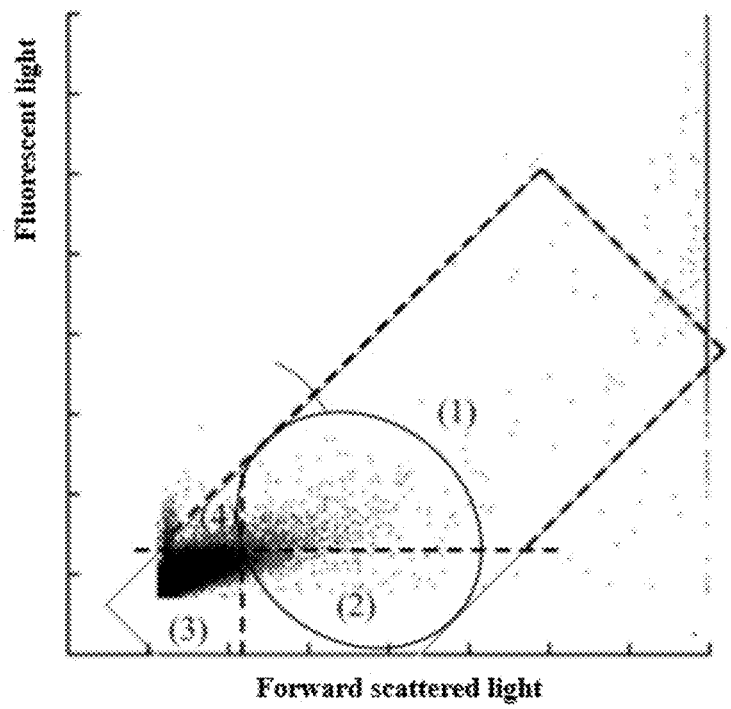
FIG. 4A is a partially enlarged view of a fluorescent light-forward scattered light scattergram of a blood sample detected by the first exemplary implementation of the present disclosure, in which a preset region for differentiating large platelets is shown.
Figure 4B:
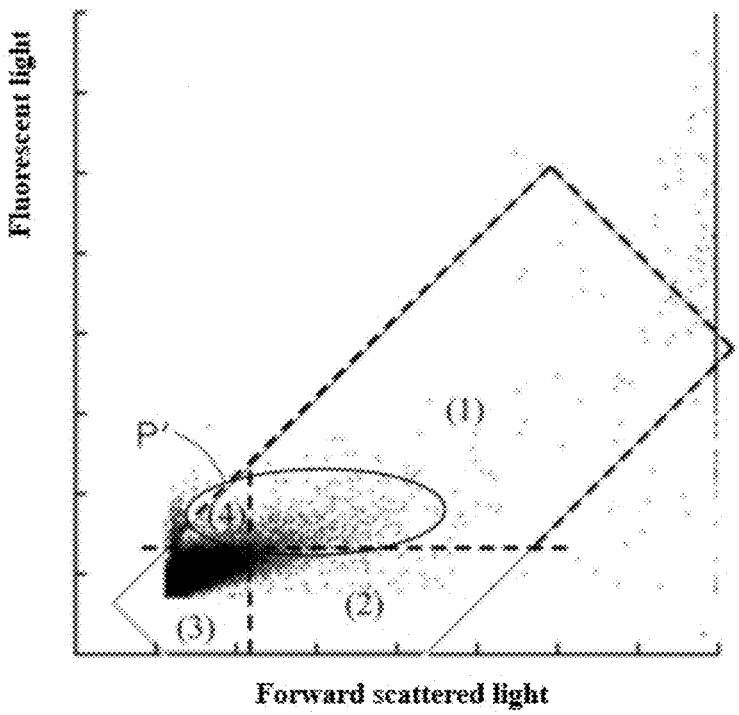
FIG. 4B is a partially enlarged view of FIG. 4A, in which a preset region for differentiating immature platelets is shown.

The inventor found after repeated assumptions and experiments that large platelets and immature platelets treated by the hemolytic agent differ in volume size and cellular content from red blood cell fragments and white blood cells, and the two types of platelet subpopulations can be differentiated in the hemolyzed blood sample by an optical method. FIG. 4A and FIG. 4B are partially enlarged views of the FL-FSC scattergram of a blood sample detected by the first exemplary implementation of the present disclosure, in which the white blood cell region in the scattergram is not shown. FIG. 4A shows an embodiment of a preset region P and a forward scattered light threshold for differentiating large platelets. FIG. 4B shows an embodiment of a preset region P' and a fluorescent light threshold for differentiating immature platelets. In FIG. 4A and FIG. 4B, the differences between the preset regions set for differentiating large platelets and immature platelets can be seen. Moreover, the inventor believes that in FIG. 4A and FIG. 4B, particles in a region, in which both fluorescent signals and forward scattered light signals are less than corresponding thresholds, include platelets with a relatively small volume and red blood cell fragments. Information about white blood cells and the platelet subpopulation can be acquired based on the at least two types of optical signals of the hemolyzed blood sample by using the methods of the present disclosure, wherein one type of the at least two types of optical signals is used to provide volume information of blood cells, and the other type is used to provide content information of blood cells.

Further, the data analysis module 70 may further comprise an alarm module 790. The alarm module 790 acquires the detection data related to the platelet subpopulation from the classification and counting module 770. The detection data related to the platelet subpopulation comprises but not limited to volume distribution data of the platelet subpopulation (for example, volume histograms of large platelets and/or immature platelets) and count value of the platelet subpopulation (for example, count of large platelets, count of immature platelets and/or count of platelets with a volume greater than 15 fL, etc.). The alarm module 790 determines whether the detection data of the platelet subpopulation is abnormal; provides an alarm if the detection data of the platelet subpopulation is determined to be abnormal; if not, finishes the process. It can be understood that the alarm module 790 may compare the detection data of the platelet subpopulation with at least one preset condition by one or more methods such as a numerical comparison and/or a graphical comparison and the like, thereby determining whether the detection data of the platelet subpopulation in the test blood sample is abnormal. The specific alarm determination method may be any method known to those skilled in the art, which will not be repeated herein.

Figure 5A:
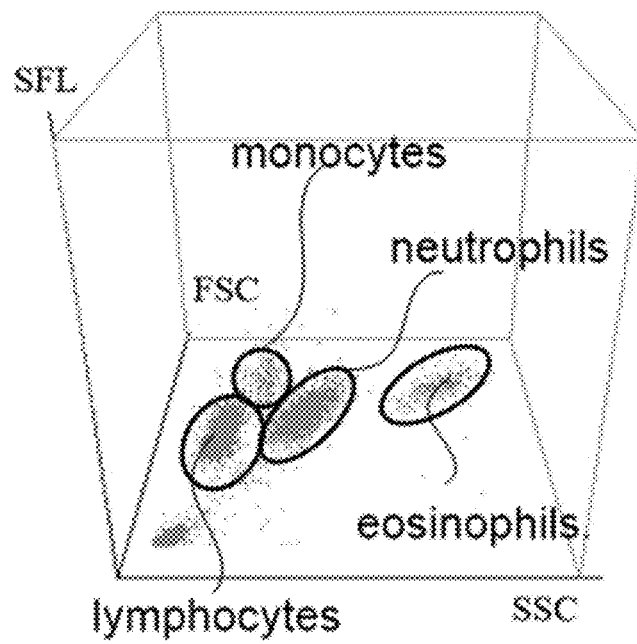
FIG. 5A is an embodiment differentiating among lymphocytes, monocytes, neutrophils and eosinophils based on a fluorescent light-forward scattered light-side scattered light scattergram of a blood sample acquired by the first exemplary implementation of the present disclosure.
Figure 5B:
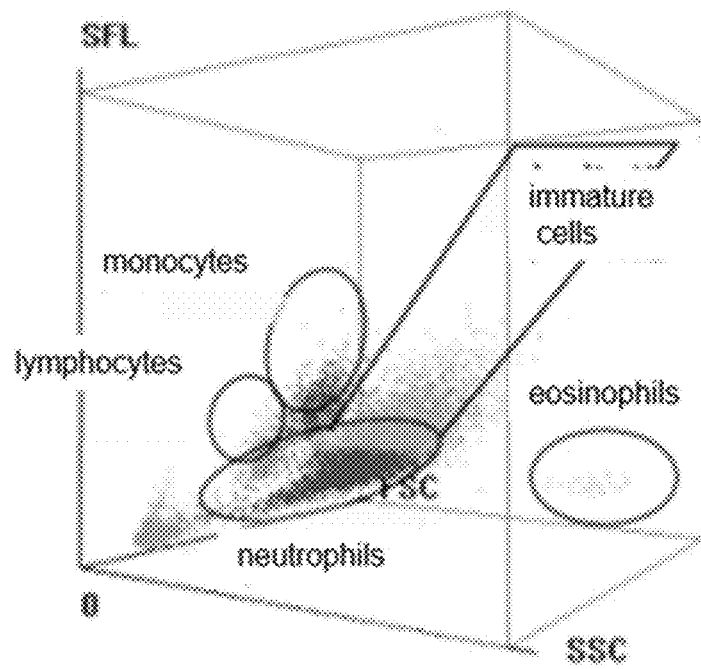
FIG. 5B is an embodiment for differentiating immature cells based on the fluorescent light-forward scattered light-side scattered light scattergram of the blood sample acquired by the first exemplary implementation of the present disclosure.

Those skilled in the art should understand that the blood analysis system 1 provided by the first exemplary implementation may further classify white blood cells, count white blood cells, and identify nucleated red blood cells, immature cells and/or blast cells. The classification and counting module 770 may classify white blood cell subpopulations based on the scattered light signals and the fluorescent signals of the white blood cell region W in the scattergram. In an embodiment, the classification and counting module 770 classifies and counts neutrophils, lymphocytes, monocytes and eosinophils, based on the particle populations appeared in the white blood cell region W, for example, as shown in FIG. 5A. Alternatively, the classification and counting module 770 may further differentiate and/or count basophils. Alternatively, the classification and counting module 770 may acquire a count of white blood cells of the test blood sample. Those skilled in the art should understand that the blood analysis system 1 provided by the first exemplary implementation may further identify nucleated red blood cells, immature cells or blast cells. For example, as shown in FIG. 5B, when immature cells exist in the blood sample, based on the scattered light signals and the fluorescent signals, immature cells can further be identified, and white blood cells can be classified into four subpopulations: lymphocytes, monocytes, neutrophils and eosinophils.

In the first exemplary implementation of the present disclosure, the user interface 90 of the blood analysis system 1 is a medium for interaction and information exchange between the blood analysis system and users. The data analysis module 70 transmits the detection data of the platelet subpopulation, such as its volume distribution data, its count value, etc., to the user interface 90, thereby presenting detection results of the test blood sample to users of the blood analysis system. In an embodiment, the user interface 90 may be a touch screen, which can identify touch control operations from users and display detection results. In another embodiment, the user interface 90 may comprise an input device and an output device. The input device may be a data input medium which is electrically connected with the data analysis module 70, such as a keyboard, a mouse, a microphone and the like. The output device may be a display screen, a printer, a speaker, an indicator light and the like. It can be understood that, for the blood analysis system provided with alarm module 790, its alarming method is to specifically mark the blood sample in a detection report or a displayed detection image, or to prompt users by flashing, sound or other manners.

It should be noted that the detection data of the platelet subpopulation displayed by the user interface 90 may either be a numerical count value or a graphical volume histogram. Except for displaying the detection data of the platelet subpopulation, the user interface 90 may further display the information obtained in the intermediate steps of the classification and counting module 770, wherein the information comprises but not is limited to the scattergram of the at least two optical signals, an image displaying the white blood cell region W in the scattergram, an image displaying the preset region P in the scattergram, an image with an enlarged view of the preset region P and its surrounding regions in the scattergram, analysis results and/or images of other blood cells, etc. The displayed blood analysis information may be displayed in various manners, for example, displayed with analysis results of other blood cells in the test blood sample, displayed in a preset region of the display screen, displayed in a hierarchical manner so that the users can select specific displays according to their interests, and displayed in other alternative manners.

Alternatively, in the first exemplary implementation of the present disclosure, the optical detector 536 of the sample detection device 50 may be set as being suitable for detecting the forward scattered light signals, the side scattered light signals and the fluorescent signals of the first test sample when the first test sample passes through the optical flow chamber 532. In other words, the at least two types of optical signals comprise forward scattered light signals, side scattered light signals and fluorescent signals. It can be understood that in this case, the signal acquisition module 750 can acquire the forward scattered light signals, the side scattered light signals and the fluorescent signals of the first test sample; the classification and counting module 770 generates the scattergram of the first test sample based on the forward scattered light signals, the side scattered light signals and the fluorescent signals, differentiates between the white blood cell region and the preset region in the scattergram, and acquires the detection data of the platelet subpopulation in the blood sample based on the preset region in the scattergram. The scattergram may be a fluorescent light-forward scattered light 2D scattergram, a fluorescent light-side scattered light 2D scattergram or a forward scattered light-side scattered light 2D scattergram, and may be a fluorescent light-forward scattered light-side scattered light 3D scattergram. The intensities of the forward scattered light signals of the preset region are substantially less than that of the white blood cell region. The intensities of the side scattered light signals of the preset region are substantially less than that of the white blood cell region. The intensities of the fluorescent signals of the preset region are substantially less than that of the white blood cell region.

In case that the at least two types of optical signals comprise side scattered light signals, the classification and counting module 770 can not only calculate the volume distribution data of the platelet subpopulation by Equations (1), Equation (2) or Equation (3) based on the forward scattered light signals of the preset region P, but can also calculate the volume of each particle in the large platelet region PG based on the forward scattered light signals and the side scattered light signals of the preset region P by using the Mie Scattering Theory (ZHANG Wei, LU Yuan, DU Shiming, et. al., Analysis on Mie Scattering Characteristics of Spherical Particles, Optical Technology, 2010-11: Volume 36 Issue 6: 936-939.), thereby acquiring the volume distribution data of the platelet subpopulation.

Further, when the data analysis module 70 can acquire a count of platelets in the test blood sample, the classification and counting module 770 can calculate a ratio of the platelet subpopulation in the test blood sample based on the detection data of the platelet subpopulation and the count of platelets. When the detection data of the platelet subpopulation is volume distribution data, the classification and counting module 770 can calculate a count value of the platelet subpopulation based on the volume distribution data. Specifically, when the platelet subpopulation is large platelet subpopulation, Platelet Large Cell Ratio (P-LCR) can be acquired by calculating a ratio of the count of large platelets to the count of platelets in the test blood sample; when the platelet subpopulation is immature platelet subpopulation, Immature Platelet Fraction (IPF %) can be acquired by calculating a ratio of the count of immature platelets to the count of platelets in the test blood sample, that is, Immature Platelet Fraction (IPF %)=the count of immature platelets (IPF)/the count of platelets (PLT). In addition, since the classification and counting module 770 can count platelets with a volume greater than a preset volume threshold based on the volume distribution data of the platelet subpopulation, the classification and counting module 770 can also acquire a ratio of platelets within a specific volume range.

Figure 6:
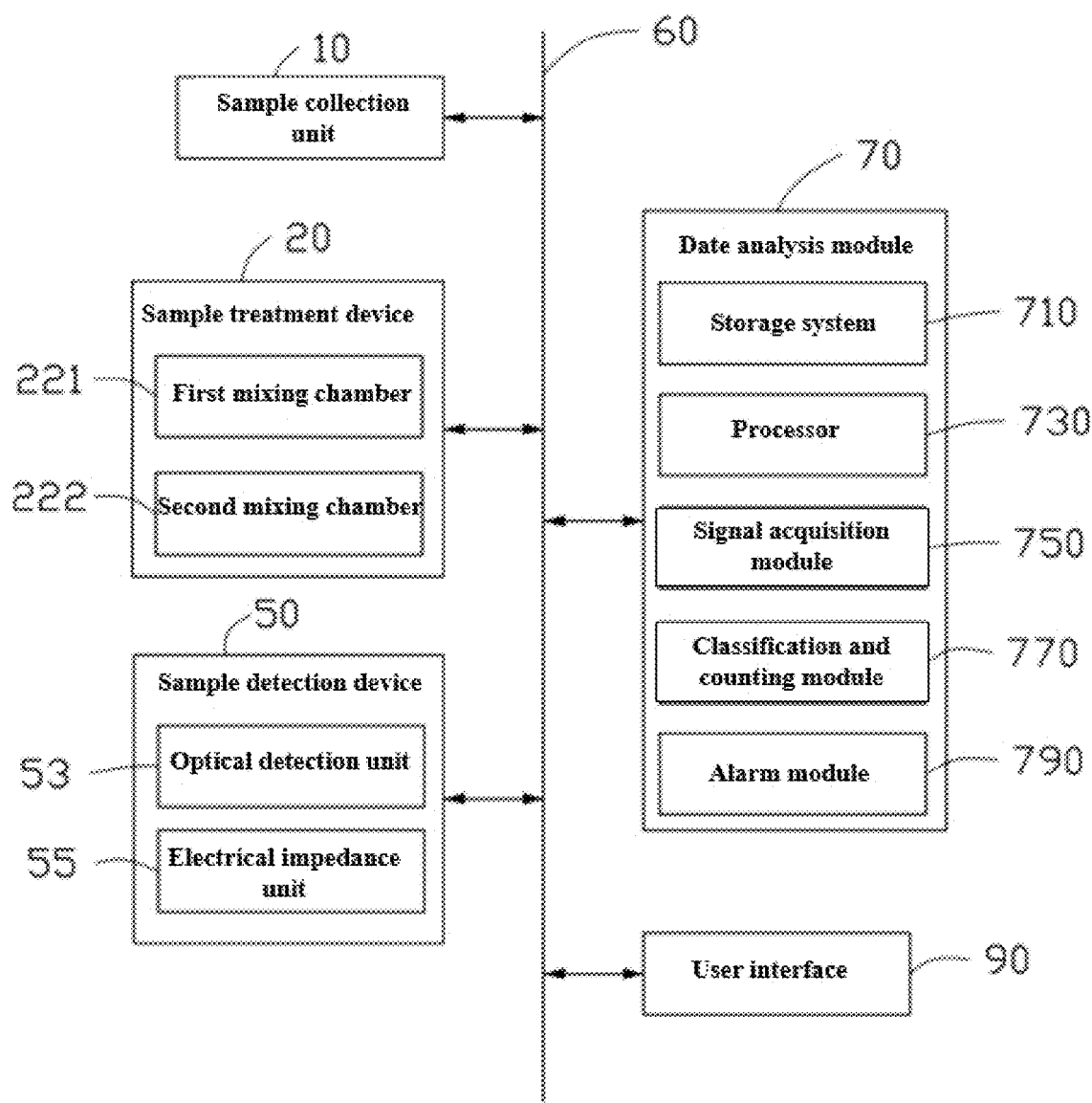
FIG. 6 is a schematic diagram of function modules of a blood analysis system provided by a second exemplary implementation of the present disclosure.

In a second exemplary implementation of the present disclosure, the blood analysis system may further comprise corresponding structures and function modules for electrical impedance detection, thereby providing detection data based on the electrical impedance detection, such as the count of platelets. FIG. 6 is a schematic diagram of a blood analysis system 2. The differences between the blood analysis system 2 and the blood analysis system 1 in the first exemplary implementation described above will be described in detail below. For other same or similar structures and functions, reference is made to the description of the blood analysis system 1 above, which will not be repeated herein.

In order to provide electrical impedance detection data, the sample treatment device 20 of the blood analysis system 2 mixes a second aliquot of the test blood sample with a diluent agent to prepare a second test sample. Alternatively, the sample treatment device 20 comprises a first mixing chamber 221 and a second mixing chamber 222 to respectively prepare the first test sample and the second test sample. As shown in FIG. 6, the sample detection device 50 of the blood analysis system 2 further comprises an electrical impedance detection unit 55. The electrical impedance detection unit comprises an aperture and an electrical impedance detector, wherein the electrical impedance detector is configured to detect electrical impedance signals of the second test sample passing through the aperture. The signal acquisition module 750 of the data analysis module 70 acquires the electrical impedance signals of the second test sample, and then the classification and counting module 770 acquires the count of platelets in the test blood sample based on the electrical impedance signals. Alternatively, the data analysis module 70 can further correct the count of platelets acquired by electrical impedance method by using the detection data of the platelet subpopulation to acquire a corrected count of platelets.

Similar to the first exemplary implementation described above, the optical detection unit 53 of the blood analysis system 2 can provide at least two types of optical signals of the first test sample after hemolysis and fluorescent staining of the test blood sample, and the classification and counting module 770 can acquire the detection data of the platelet subpopulation based on the at least two types of optical signals. Thus, the classification and counting module 770 can calculate the ratio of the platelet subpopulation based on the detection data of the platelet subpopulation and the count of platelets (or corrected count of platelets).

Figure 7:
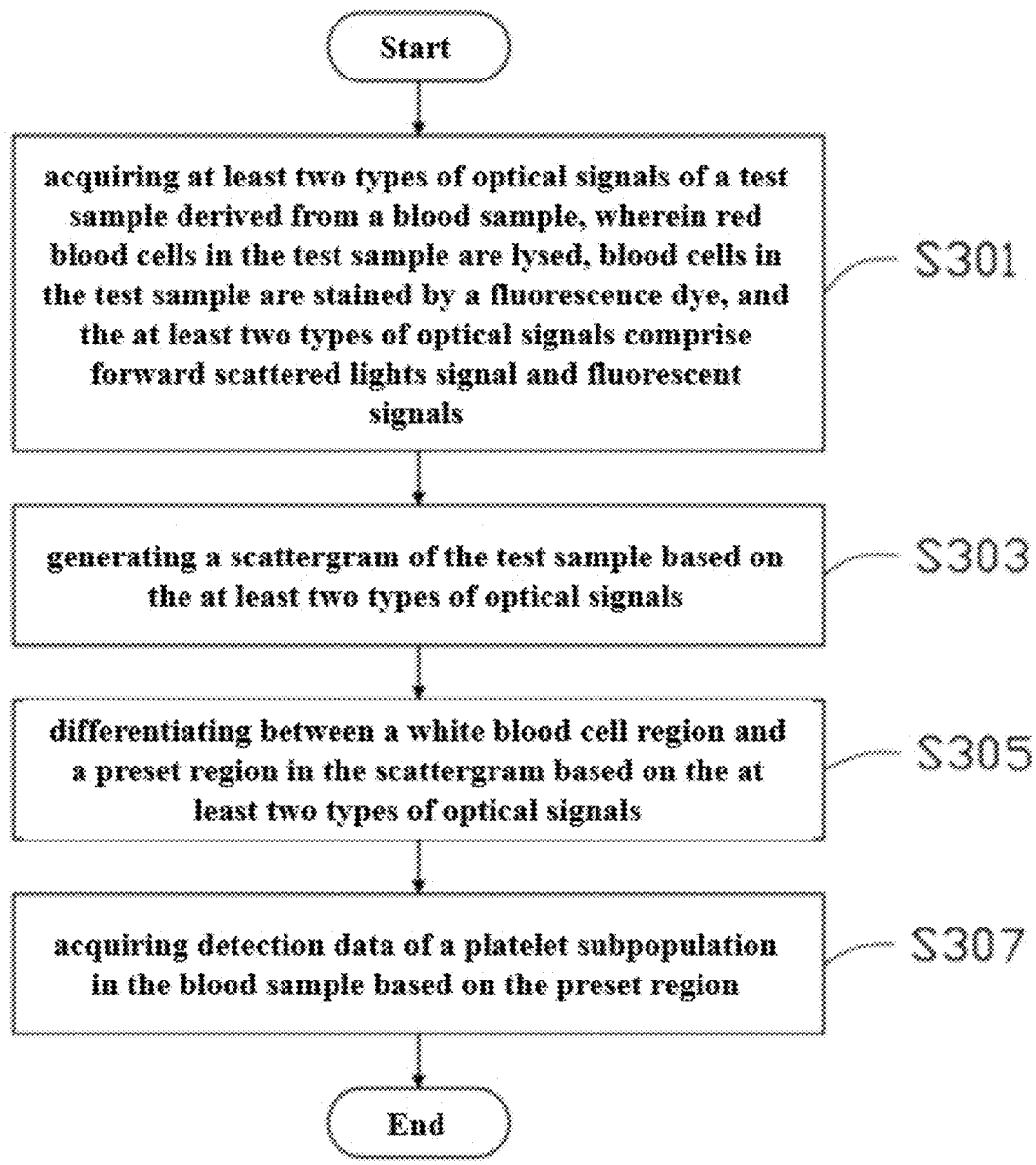
FIG. 7 is a flowchart of an analysis method of a blood sample provided by a third exemplary implementation of the present disclosure.

Corresponding to the first exemplary implementation of the present disclosure, a third exemplary implementation mode of the present disclosure provides an analysis method for blood sample. The analysis method for blood sample may be used in a flow cytometer or any automated blood analysis system described in the first and second exemplary implementations. The analysis method for blood sample may be implemented by a processor in the form of computer programs. The computer programs may be arranged in a flow cytometer or an automated blood analyzer, or may be independently arranged in a computer that directly or indirectly acquires blood cell detection signal data. The analysis method for blood sample comprises the following steps, as shown in FIG. 7.

Step S301: acquiring at least two types of optical signals of a test sample derived from a blood sample, wherein red blood cells in the test sample are lysed, blood cells in the test sample are stained by a fluorescence dye. The at least two types of optical signals comprise forward scattered light signals and fluorescent signals.

Step S303: generating a scattergram of the test sample based on the at least two types of optical signals.

Step S305: differentiating between a white blood cell region and a preset region in the scattergram based on the at least two types of optical signals.

Step S307: acquiring detection data of a platelet subpopulation in the blood sample based on the preset region. It can be understood that, before step S301, the test sample is prepared by mixing the test blood sample with a lytic reagent under certain reaction conditions. The lytic reagent comprises a hemolytic agent for lysing red blood cells, and a fluorescence dye for staining blood cells. For descriptions of the hemolytic agent and the fluorescence dye, reference is made to the contents above, which will not be repeated herein. The preparation process of the test sample may be automatically, semi-automatically, or manually implemented. Then, the forward scattered light signals and the fluorescent signals of the test sample are detected by an optical detection unit of a flow cytometer or a blood analysis system.

In the third exemplary implementation, at step S301, the forward scattered light signals and the fluorescent signals of the test sample are acquired from the optical detection unit. At step S303, a fluorescent light-forward scattered light scattergram of the test sample is generated based on the forward scattered light signals and the fluorescent signals. At step S305, the white blood cell region W and the preset region P are differentiated in the scattergram based on differences in the forward scattered light signals and the fluorescent signals of different particle populations in the test sample, wherein the preset region P is a region where the platelet subpopulation (such as large platelets or immature platelets) appears in the scattergram. The intensities of the forward scattered light signals of the preset region P are substantially less than that of the white blood cell region W, the intensities of the fluorescent signals of the preset region P are substantially less than that of the white blood cell region W, and there are differences between the preset region set for differentiating large platelets and the preset region set for differentiating immature platelets. For the contents related to differentiating the preset region P, reference may be made to the related contents in the first implementation above, which will not be repeated herein.

At step S307, the detection data of the platelet subpopulation in the blood sample is acquired based on the preset region P. In an implementation, at step S307, the volume (Vol) of each particle in the preset region P is calculated by using Equation (1), Equation (2) or Equation (3) based on the forward scattered light signals of a particle population characterized in the preset region P, thereby acquiring volume distribution data of the platelet subpopulation in the test blood sample. Further, a count value of the platelet subpopulation and/or a count value of platelets within a specific volume range may be calculated based on the volume distribution data of the platelet subpopulation. Alternatively, volume distribution characteristic parameters of the platelet subpopulation, such as a volume distribution width and the like, may further be calculated based on the volume distribution data of the platelet subpopulation. In another implementation, at step S307, a number of particles (or referred to as "event number") of the particle population characterized in the preset region P is acquired, and a count value of the platelet subpopulation in the blood sample is acquired based on the number of particles.

Alternatively, when the at least two types of optical signals acquired at step S301 comprise side scattered light signals, a 2D or a 3D scattergram of the test sample may be generated based on the forward scattered light signals, the side scattered light signals and the fluorescent signals at step S303. And then, at step S305, the white blood cell region W and the preset region P are differentiated in the scattergram based on the differences in the optical signals of different particle populations in the test sample. At step S307, the volume distribution data of the platelet subpopulation may be calculated by Equations (1), Equation (2) or Equation (3) based on the forward scattered light signals of the preset region P, or the volume distribution data of the platelet subpopulation may also be calculated by using the Mie Scattering Theory based on the forward scattered light signals and the side scattered light signals of the preset region P, or the count value of the platelet subpopulation may be acquired based on the number of particles of the particle population characterized in the preset region P.

Further, the method provided by the third exemplary implementation may comprise step S308. At step S308, a count of platelets in the test blood sample is acquired, and a ratio of the platelet subpopulation is calculated based on the detection data of the platelet subpopulation acquired at step S307 and the count of platelets. It can be understood that the ratio of the platelet subpopulation is also a presentation form for the detection data of the platelet subpopulation. The count of platelets in the test blood sample may be a count of platelets measured by electrical impedance detection.

Further, the method provided by the third exemplary implementation may further comprise step S309a. At step S309a, it is determined whether the detection data of the platelet subpopulation acquired at step S307 (and/or S308) is abnormal or not; and if the detection data of the platelet subpopulation is determined to be abnormal, an alarm is provided. At step S309a, the detection data of the platelet population may be compared with at least one preset condition by using one or more methods such as a numeric comparison and/or a graphical comparison and the like, thereby determining whether the detection data of the platelet subpopulation in the test blood sample is possibly abnormal. The detection data of the platelet subpopulation may be one or more selected from count of large platelets, count of immature platelets, volume histogram of large platelets, volume histogram of immature platelets, P-LCR, IPF, and volume distribution width of large platelets.

Further, the method provided by the third exemplary implementation may further comprise step S309b. At step S309b, the detection data of the platelet subpopulation acquired at step S307 (and/or S308) are outputted. The detection data may be numerical values reflecting distribution and/or quantity characteristic of the platelet subpopulation, or graphical volume histograms of the platelet subpopulation. Alternatively, at step S308b, at least two types of optical signal data of the particle population characterized in the preset region P acquired at step S305 may also be outputted. Alternatively, at step S308b, one or more of the scattergram acquired at step S305, the scattergram with the preset region P being marked, and the partially enlarged view of the preset region P and its surrounding regions in the scattergram may also be outputted.

Further, the method provided by the third exemplary implementation may further comprise step S306. At step S306, other blood cells, including but not limited to, white blood cells, nucleated red blood cells, immature cells and blast cells, are classified and counted based on the scattergram acquired at step S305. For example, at step S306a, the white blood cell region W in the scattergram may be further classified into white blood cell subpopulations based on the at least two types of optical signals. In an embodiment, at step S306a, neutrophils, lymphocytes, monocytes and eosinophils are classified and counted. In another embodiment, at step S306b, basophils are further differentiated and/or counted. In another embodiment, at step S306c, a count of white blood cells in the test blood sample is acquired. Those skilled in the art should understand that the method of the third exemplary implementation may comprise any existing steps for analyzing blood cells based on flow cytometers.

Those skilled in the art should understand that all or part of the steps of the third exemplary implementation may also be implemented by instructing related hardware of a blood analyzer through computer programs. The computer programs may be stored in a computer-readable storage medium and loaded into the blood analyzer having corresponding hardware system. When the computer programs are executed by a processor, the blood analyzer executes the analysis method for blood sample disclosed in the third exemplary implementation of the present disclosure.

The present disclosure further provides a blood analyzer. The blood analyzer comprises a processor and a non-volatile computer-readable storage medium. The processor is configured to execute computer programs stored in the non-volatile computer-readable storage medium so as to implement the steps of the analysis method of the third exemplary implementation. For the specific steps, reference is made to various implementations and embodiments described above, which will not be repeated herein.

The present disclosure further provides a non-volatile computer-readable storage medium with computer programs stored thereon, wherein the computer programs, when executed by a processor, implement the steps of the analysis method of the third exemplary implementation. For the specific steps, reference is made to various implementations and embodiments described above, which will not be repeated herein. Therefore, the analysis method of the third exemplary implementation may be implemented in the form of software function units and sold or used as an independent product.

The blood analysis system provided by the first aspect of the present disclosure can detect at least one platelet subpopulation by using hemolysis and white blood cell detection channel and lytic reagents (for example, DIFF channel of BC-6800 blood analyzer produced by Shenzhen Mindray Bio-Medical Electronics Co., Ltd.) based on the existing five-classification blood analysis system, thereby acquiring the count and/or the volume distribution data of the platelet subpopulation, and even the ratio of the platelet subpopulation. In the blood analysis system, the analysis method, the blood analyzer and the storage medium provided by the first aspect of the present disclosure, there is no need to use a separate detection channel and a detection reagent, which can provide users with more information about platelets and their subpopulations of the test blood sample without increasing costs of the blood analysis system and costs of the reagents in the blood analysis process.

The second aspect of the present disclosure provides a blood analysis system, method, a blood analyzer and a storage medium for analyzing large platelets in a blood sample.

Refer to FIG. 1 again, a fourth exemplary implementation of the present disclosure provides a blood analysis system, which comprises a sample collection unit 10, a sample treatment device 20, a sample detection device 50, a data analysis module 70 and a user interface 90. Structure modules and function modules of the blood analysis system and the relationship between them are basically the same as those of the first exemplary implementation described above, which will not be repeated herein. The differences between the fourth exemplary implementation and the first exemplary implementation described above will be described below in detail.

In the fourth exemplary implementation of the present disclosure, the sample treatment device 20 comprises at least one mixing chamber 210, which is configured to mix a test blood sample with a lytic reagent under certain reaction conditions to prepared a first test sample. In the implementation, the lytic reagent comprises a hemolytic agent for lysing red blood cells. The hemolytic agent may be any one of existing hemolytic agents for classifying white blood cells by automated blood analyzers, for example may be any one of a cationic surfactant, a nonionic surfactant, an anionic surfactant and an amphiphilic surfactant or any combination thereof.

The sample detection device 50 comprises an optical detection unit 53. The optical detection unit 53 comprises a sheath flow system, an optical flow chamber 532, a light source 534, an optical detector 536 and a corresponding detection circuit. The optical flow chamber 532 is operatively in fluid communication with the mixing chamber 210, so that the first test sample is transferred by the sheath flow system from the mixing chamber 210 to the optical flow chamber 532. The light source 534 is configured to direct a light beam to the optical flow chamber 532. The optical detector 536 is suitable for detecting at least two types of optical signals of the first test sample when the first test sample passes through the optical flow chamber 532.

In the fourth exemplary implementation, the at least two types of optical signals comprise first scattered light signals and second scattered light signals, wherein the first scattered light signals are forward scattered light signals, and the second scattered light signals are at least one type of medium-angle scattered light signals and side scattered light signals. The medium-angle scattered light signals may be detected by a light detector at an angle between forward scattered light and side scattered light. The medium-angle scattered light signals may be low medium-angle scattered light signals detected at an angle of around 8°-24° with respect to the incident light beam, or high medium-angle scattered light signals detected at an angle of around 25°-65° with respect to the incident light beam. As mentioned above, the forward scattered light signals may be detected at an angle of around 1°-10° with respect to the incident light beam, or may be detected at an angle of around 2°-6° with respect to the incident light beam. The side scattered light signals may be detected at an angle of around 90° with respect to the incident light beam, or may be detected at an angle of around 65°-115° with respect to the incident beam.

The data analysis module 70 further comprises a signal acquisition module 750 and a classification and counting module 770. The signal acquisition module 750 is operatively connected with one or more optical detectors 536 of the sample detection device 50 to acquire the at least two types of optical signals of the first test sample. In a specific implementation of the fourth exemplary implementation, the at least two types of optical signals may be forward scattered light signals and side scattered light signals, or may be forward scattered light signals and medium-angle scattered light signals, or may be forward scattered light signals, side scattered light signals and medium-angle scattered light signals. It can be understood that either the side scattered light signals or the medium-angle scattered light signals can provide information about cellular content. The classification and counting module 770 generates a scattergram of the first test sample based on the at least two types of optical signals, differentiates between a white blood cell region and a large platelet region in the scattergram, and acquires detection data of large platelets in the blood sample based on the large platelet region in the scattergram.

Figure 8:
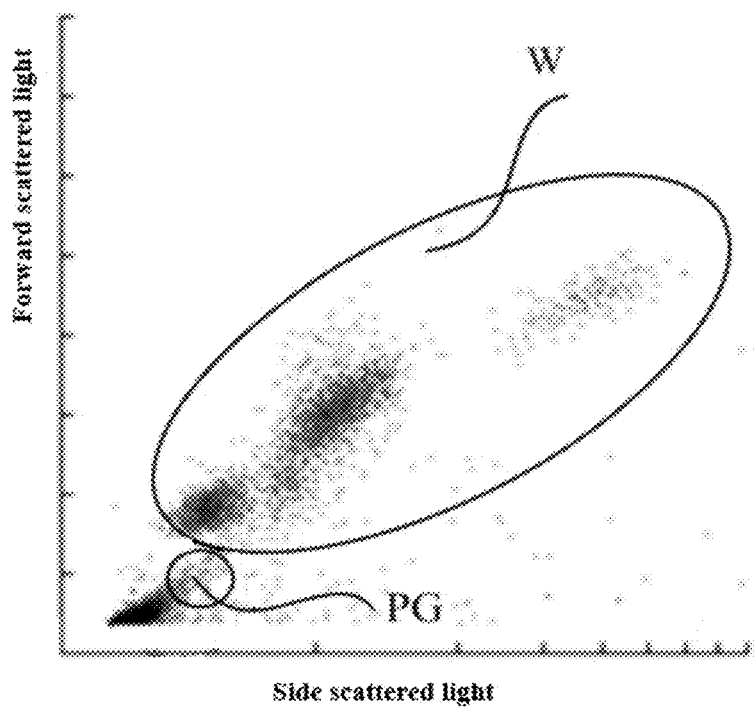
FIG. 8 is a forward scattered light-side scattered light scattergram of a blood sample acquired by a fourth exemplary implementation of the present disclosure.

Specifically, taking the at least two types of optical signals including forward scattered light signals and side scattered light signals as an example, the classification and counting module 770 generates a forward scattered light-side scattered light scattergram of the first test sample. The scattergram may be a 2D scattergram with the intensities of the side scattered light signals of the first test sample as abscissa and the intensities of the forward scattered light signals of the first test sample as ordinate, as shown in FIG. 8. It can be understood that when the at least two types of optical signals further comprise other optical signals (such as medium-angle scattered light signals and fluorescent signals), the scattergram may also be a 3D scatter diagram. It can be understood that the abscissa and ordinate of the scattergram may also be other parameters of the forward scattered light signals and the side scattered light signals that reflect particle characteristics of the first test sample, and the abscissa and ordinate of the scattergram may also be non-linear coordinate axis, such as logarithmic coordinate axis, to further highlight differences in distribution between the particle populations.

In the embodiment shown in FIG. 8, the classification and counting module 770 differentiates between the white blood cell region W and the large platelet region PG in the scattergram, based on the differences in the intensities of the forward scattered light signals and the side scattered light signals of the first test sample, wherein the large platelet region PG is a region where large platelets appear in the scattergram. Those skilled in the art should understand that the white blood cell region W and the large platelet region PG may be set by gating technique. As shown in FIG. 8, it is generally well known to those skilled in the art that particles within a region with smaller FSC intensities and smaller SSC intensities in the scattergram are mainly red blood cell fragments. The inventor found after repeated assumptions and experiments that large platelets treated by the hemolytic agent differ in volume size and cellular content from red blood cell fragments and white blood cells, and large platelets can be differentiated in the hemolyzed blood sample by an optical method. As shown in FIG. 8, the intensities of the forward scattered light signals of the large platelet region PG are substantially less than that of the white blood cell region W and are substantially greater than that of red blood cells at the lower left corner of the scattergram. The intensities of the side scattered light signals of the large platelet region PG are substantially less than that of the white blood cell region W and are substantially greater than that of red blood cells at the lower left corner of the scattergram. Those skilled in the art should understand that the large platelet region PG may be located at a fixed position in the scattergram, or may be determined according to the position of W.

The classification and counting module 770 may acquire the detection data of large platelets in the test blood sample based on a particle population characterized in the large platelet region PG in the scattergram. The classification and counting module 770 acquires volume distribution data of large platelets based on the forward scattered light signals of the particle population characterized in the large platelet region PG. Specifically, the forward scattered light signals may be converted respectively into a volume of each particle in the large platelet region PG by using Equation (1), Equation (2) or Equation (3), thereby acquiring the volume distribution data of large platelets. When the second scattered light signals are side scattered light signals, the classification and counting module 770 may also calculate the volume of each particle in the large platelet region PG based on the forward scattered light signals and the side scattered light signals of the particle population characterized in the large platelet region PG by using the Mie Scattering Theory, thereby acquiring the volume distribution data of large platelets. The volume distribution data may be presented in a numerical form or a graphical form, such as a volume histogram.

Further, a count value of large platelets may further be calculated based on the volume distribution data of large platelets. In the present disclosure, a volume threshold for defining large platelets may be set by users, and the large platelets may be platelets with a volume greater than 10 fL, 12 fL, 15 fL or 20 fL, or may be platelets with a volume greater than any value between 10-20 fL. Those skilled in the art should understand that the range of the large platelet region PG may accordingly be changed based on the set volume threshold of large platelets. Alternatively, volume distribution characteristic parameters of large platelets, such as volume distribution width and the like, may further be calculated based on the volume distribution data of large platelets.

Alternatively, the classification and counting module 770 may also acquire the number of particles (or referred to as "event number") of the particle population characterized in the large platelet region PG and the count value of large platelets in the blood sample based on the number of particles.

Further, when the data analysis module 70 may acquire a count of platelets in the test blood sample, the classification and counting module 770 may calculate a ratio of large platelets (P-LCR) in the test blood sample based on the detection data of large platelets and the count of platelets. The count of platelets in the test blood sample may be acquired through optical method or electrical impedance method, which can be seen from above and will not be repeated herein.

Figure 9:
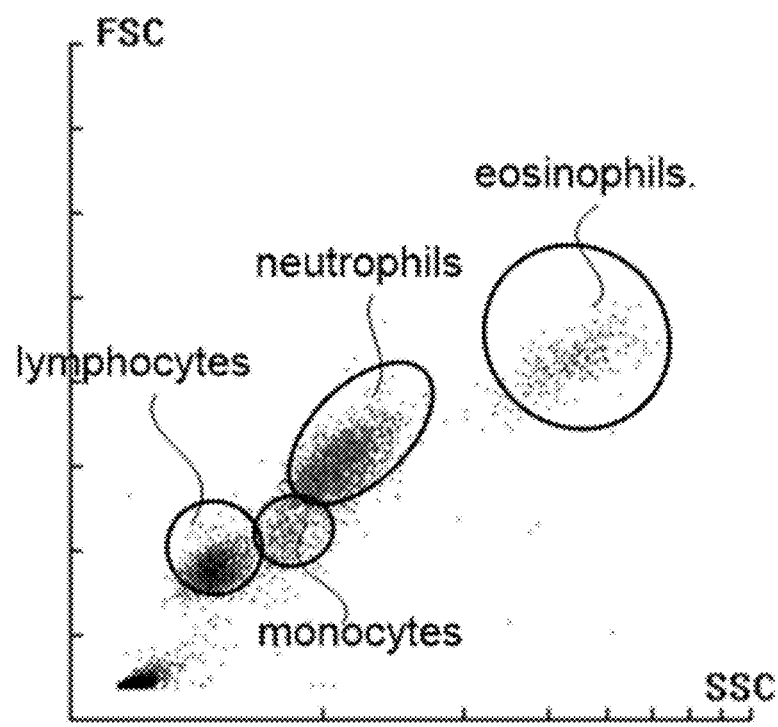
FIG. 9 is an embodiment for differentiating white blood cell subpopulations based on the forward scattered light-side scattered light scattergram of the blood sample acquired by the fourth exemplary implementation of the present disclosure.

In the fourth exemplary implementation, the classification and counting module 770 may further classify and count other blood cells, including but not limited to, white blood cells, nucleated red blood cells, immature cells and blast cells, based on the scattergram (for example, forward-side scattered light scattergram, forward-medium-angle scattered light scattergram, forward-side-medium-angle light scattergram, etc.) generated by the two types of optical signals. In the embodiment shown in FIG. 9, the classification and counting module 770 further differentiates white blood cell subpopulations in the white blood cell region W of the forward-side scattered light scattergram. In the embodiment, the classification and counting module 770 classifies and counts neutrophils, lymphocytes, monocytes and eosinophils. It can be understood that in another embodiment, the classification and counting module 770 may also classify and count basophils. In another embodiment, the classification and counting module 770 may also acquire a count of white blood cells in the test blood sample.

One or more of analysis results and intermediate results acquired by the classification and counting module 770, such as the detection data of large platelets, the scattergram, the data of the particle population characterized in the large platelet region PG in the scattergram and the scattergram with the large platelet region being marked, may be outputted to the user interface 90. The analysis results and intermediate results may be presented in a numerical form, in a graphical form, or in a form of a specific blood analysis report with combination of numbers, words and/or graphics.

In the fourth exemplary implementation, the data analysis module 70 may further comprise an alarm module 790. The alarm module 790 acquires the detection data of large platelets from the classification and counting module 770, including but not limited to, one or more of: count value of large platelets, volume histogram of large platelets, volume distribution width of large platelets and P-LCR. The alarm module 790 determines whether the detection data of large platelets is abnormal; if yes, an alarm is provided; if not, the process ends.

Figure 10:
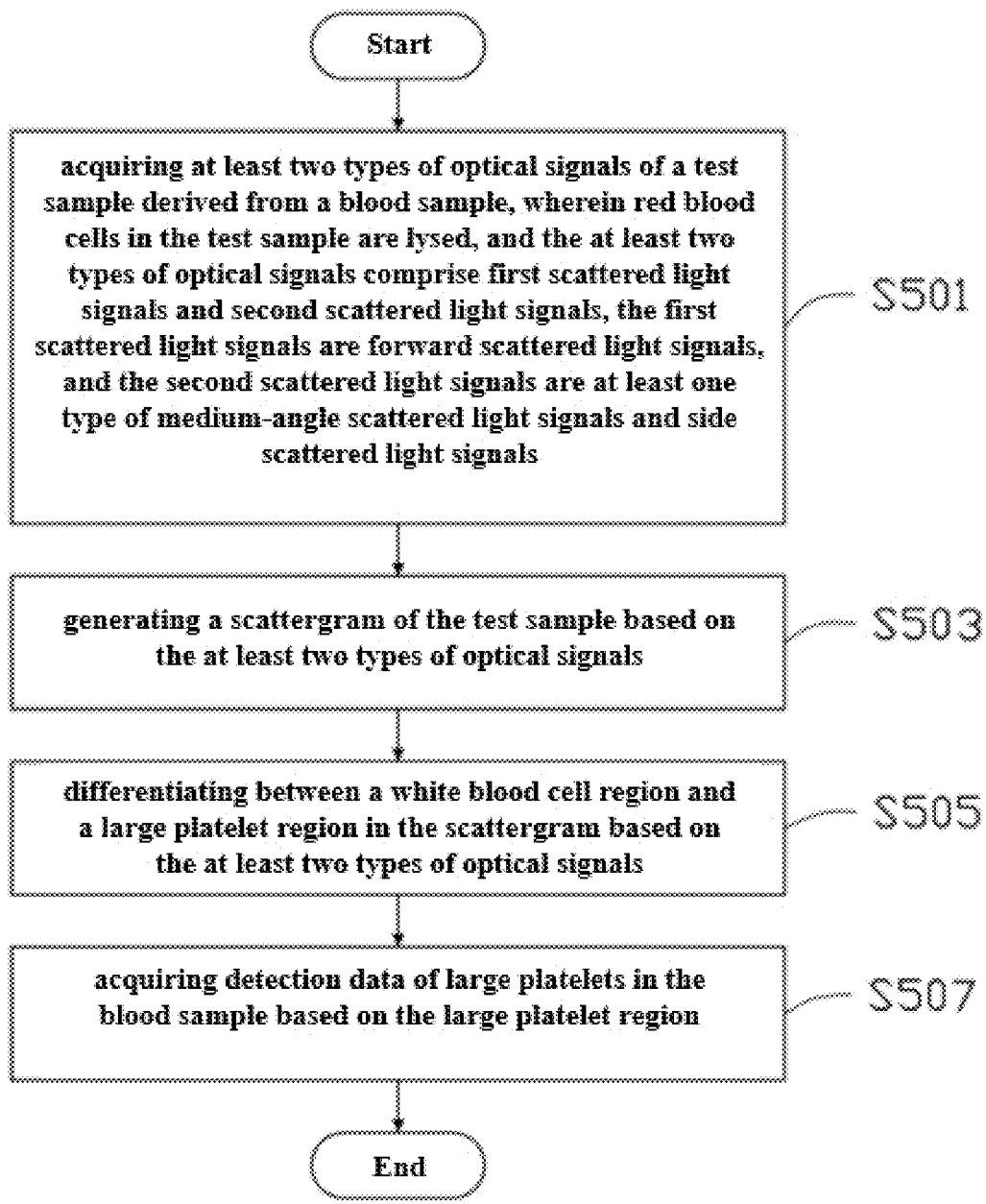
FIG. 10 is a flowchart of an analysis method of a blood sample provided by a fifth exemplary implementation of the present disclosure.

Corresponding to the fourth exemplary implementation of the present disclosure, a fifth exemplary implementation of the present disclosure provides an analysis method for blood sample. The analysis method for blood sample may be used in a flow cytometer or any automated blood analysis system provided by the fourth exemplary implementation. The analysis method for blood sample comprises the following steps, as shown in FIG. 10.

Step S501: acquiring at least two types of optical signals of a test sample derived from a blood sample. Red blood cells in the test sample are lysed. The at least two types of optical signals comprise first scattered light signals and second scattered light signals, the first scattered light signals are forward scattered light signals, and the second scattered light signals are at least one type selected from medium-angle scattered light signals and side scattered light signals.

Step S503: generating a scattergram of the test sample based on the at least two types of optical signals;

Step S505: differentiating between a white blood cell region and a large platelet region in the scattergram based on the at least two types of optical signals.

Step S507: acquiring detection data of large platelets in the blood sample based on the large platelet region.

It can be understood that, before step S501, the test sample may be prepared by mixing the test blood sample with a lytic reagent under certain reaction conditions, and the lytic reagent comprises a hemolytic agent for lysing red blood cells. For descriptions of the hemolytic agent and the fluorescence dye, reference may be made to the corresponding contents above, which will not be repeated herein. The preparation process of the test sample may be automatically, semi-automatically, or manually implemented. Then, the forward scattered light signals and the side scattered light signals (or the medium-angle scattered light signals) of the test sample are detected by an optical detection unit of a flow cytometer or a blood analysis system.

In the fifth exemplary implementation, at step S501, the at least two types of optical signals of the test sample are acquired from the optical detection unit, for example, the forward scattered light signals and the side scattered light signals, or, the forward scattered light signals and the medium-angle scattered light signals. At step S503, the scattergram of the test sample is generated based on the at least two types of optical signals, for example, forward-side scattered light scattergram or forward-medium-angle scattered light scattergram. At step S505, the white blood cell region W and the large platelet region PG are differentiated in the scattergram based on the differences in the forward scattered light signals and the side scattered light signals (or the medium-angle scattered light signals) of different particle populations in the test sample. For the specific method for differentiating the large platelet region PG, reference may be made to the relevant descriptions in the fourth exemplary implementation, which will not be repeated herein.

At step S507, the detection data of large platelets in the test blood sample is acquired based on a particle population characterized in the large platelet region PG. Specifically, the forward scattered light signals may be converted respectively into a volume of each particle in the large platelet region PG by using Equation (1), Equation (2) or Equation (3), thereby acquiring volume distribution data of large platelets. When the second scattered light signals are side scattered light signals, the forward scattered light signals and the side scattered light signals of the particle population characterized in the large platelet region PG may also be converted respectively into a volume of each particle in the large platelet region PG by using the Mie Scattering Theory, thereby acquiring the volume distribution data of large platelets. The volume distribution data may be presented in a numerical form or a graphical form, such as a volume histogram. Further, at step S507, a count value of large platelets and/or other parameters that reflect volume distribution characteristics of large platelets may further be calculated based on the volume distribution data of large platelets. Alternatively, at S507, a number of particles of the particle population characterized in the large platelet region PG may also be acquired, and a count value of large platelets in the blood sample is acquired based on the number of particles.

Alternatively, the method provided by the fifth exemplary implementation may further comprise step S508. At step S508, a count of platelets in the test blood sample is acquired, and then a ratio of large platelets is calculated based on the detection data of large platelets acquired at step S507 and the count of platelets. The count of platelets in the test blood sample may be a count of platelets acquired by electrical impedance detection, or a count of platelets acquired by an optical method, or a corrected count of platelets acquired by at least two platelet counting methods. The optical method may be a platelet counting method by using a dye capable of specifically binding to platelets, or a platelet counting method by detecting scattered light at different angles, or a platelet counting method by combining the at least two types of optical signals with a specific lytic reagent.

Alternatively, the method provided by the fifth exemplary implementation may further comprise step S509a. At step S509a, it is determined whether the detection data of large platelets acquired at step S507 (and/or S508) is abnormal; if yes, an alarm is provided. Alternatively, the method provided by the fifth exemplary implementation may further comprise step S509b. At step S509b, one or more of the detection data of large platelets acquired at step S507 (and/or S508) and/or intermediate results acquired at step S507 are outputted. At step S509b, a blood analysis result in a numerical form, or a blood analysis result in a graphical form, or a specific blood analysis report with combination of numbers, words and/or graphics, may be outputted.

Further, the method provided by the fifth exemplary implementation may further comprise step S506. At step S506, other blood cells, including but not limited to, white blood cells, nucleated red blood cells, immature cells and blast cells, are classified and counted based on the scattergram acquired at step S505. At step S507, white blood cells may be classified into white blood cell subpopulations and/or white blood cells may be counted. Alternatively, classifying white blood cells into white blood cell subpopulations comprises classifying white blood cells into neutrophils, lymphocytes, monocytes and eosinophils, or classifying white blood cells into basophils.

Those skilled in the art should understand that all or part of the steps in the fifth exemplary implementation may also be implemented by instructing related hardware of a blood analyzer through computer programs. The computer programs may be stored in a computer-readable storage medium and loaded into the blood analyzer having corresponding hardware system. When the computer programs are executed by a processor, the blood analyzer executes the analysis method for blood sample disclosed in the fifth exemplary implementation of the present disclosure.

The present disclosure further provides a blood analyzer. The blood analyzer comprises a processor and a non-volatile computer-readable storage medium. The processor is configured to execute computer programs stored in the non-volatile computer-readable storage medium so as to implement the steps of the analysis method of the fifth exemplary implementation. For the specific steps, reference may be made to various implementations and embodiments described above, which will not be repeated herein.

The present disclosure further provides a non-volatile computer-readable storage medium with computer programs stored thereon, wherein the computer programs, when executed by a processor, implement the steps of the analysis method of the fifth exemplary implementation. For the specific steps, reference may be made to various implementations and embodiments described above, which will not be repeated herein. Therefore, the analysis method of the fifth exemplary implementation may be implemented in the form of software function units and sold or used as an independent product.

Compared with the first aspect of the present disclosure described above, the blood analysis system, the analysis method, the blood analyzer and the storage medium provided by the second aspect can implement the detection of large platelets without using a fluorescence dye. In some specific implementations, the blood analysis system, the analysis method, the blood analyzer and the storage medium provided by the second aspect of the present disclosure can detect large platelets by using hemolysis and white blood cell detection channel and corresponding lytic reagents (for example, DIFF channel of BC-6800 blood analyzer produced by SHENZHEN MINDRAY BIO-MEDICAL ELECTRONICS CO., LTD.) of the existing five-classification blood analysis system, thereby acquiring blood analysis results, such as the count value and/or the volume distribution data of large platelets, the ratio of large platelets and the like. The present disclosure can provide users with more information about platelets and their subpopulations of the test blood sample, without increasing costs of the blood analysis system and costs of the reagents in the blood analysis process. Those skilled in the art should understand that the second aspect may also be applied in a blood analyzer for detecting fluorescent signals, as long as the blood analyzer can detect forward scattered light signals, side scattered light signals and fluorescent signals simultaneously.

EXAMPLES

A plurality of blood samples was detected by respectively executing the analysis method provided by the present disclosure and a reference method in a BC-6800 blood cell analyzer produced by SHENZHEN MINDRAY BIO-MEDICAL ELECTRONICS CO., LTD. By comparing counts of large platelets and counts of immature platelets obtained by the method provided by the present disclosure with that obtained by the reference method, the correlations therebetween were obtained.

The steps of the reference method were as follows:

A blood samples was mixed and reacted with a reagent to obtain a test solution, and the components of the reagent were as follows:

| Fluorescence dye | 7 mg |
|---|---|
| NaH2PO4•H2O | 53.8 mg |
| Na2HPO4•7H2O | 163.4 mg |
| Cocamidopropyl betaine | 100 mg |

The components were dissolved in 1 L water, and pH was 7.

The structural formula of the fluorescence dye was

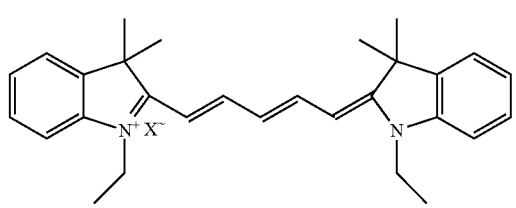

Forward scattered light signals, side scattered light signals and fluorescent signals of each cell in the test solution were detected by the BC-6800, and platelets were identified using the forward scattered light signals and the fluorescent signals, a total number of platelets was thus acquired. Based on the forward scattered light signals and the side scattered light signals of platelet particles, the volume of each platelet can be calculated by using the Mie Scattering Theory (ZHANG Wei, LU Yuan, DU Shiming, et. al., Analysis on Mie Scattering Characteristics of Spherical Particles, Optical Technology, 2010-11: Volume 36 Issue 6: 936-939.), thereby acquiring numbers of platelets with different volumes. A ratio of large platelets was acquired according to the number of large platelets and the total number of platelets.

Specifically, 82 blood samples were selected to compare the method of the present disclosure and the reference method. Among the 82 blood samples, there were 57 normal blood samples, 15 samples containing red blood cell fragments, 5 samples containing microcytes and 5 samples containing large platelets, which was confirmed by manual microscopic examination. According to the method of the present disclosure, as shown in FIG. 2A, FIG. 2B and FIG. 3, a volume histogram of platelets subjected to hemolysis was acquired by Equation (1), and information about platelets was calculated.

Figure 11:
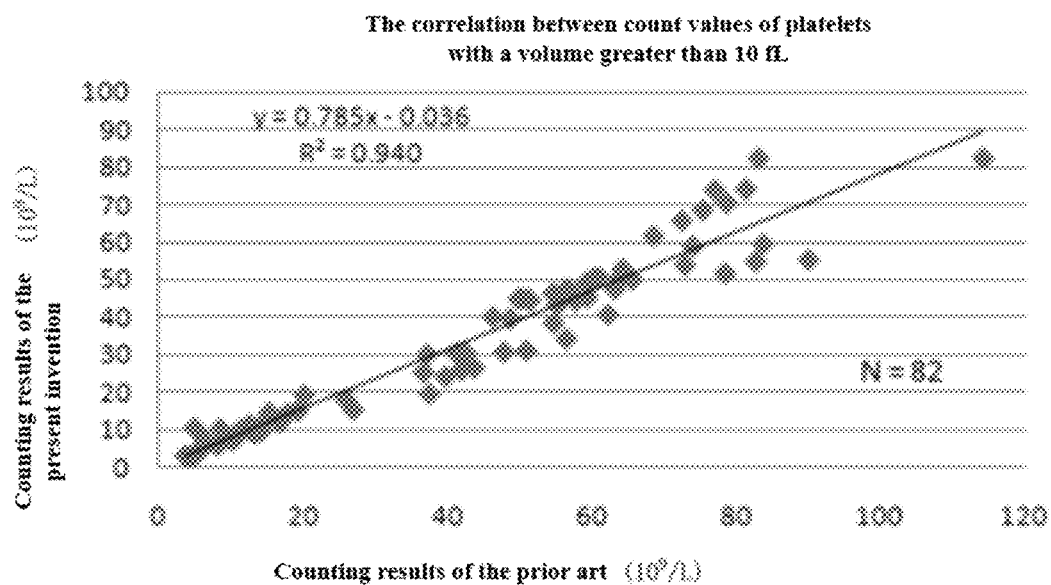
FIG. 11 shows a correlation between a count value of large platelets having a volume greater than 10 fL acquired by an implementation of the present disclosure and a count value of large platelets having a volume greater than 10 fL acquired by the prior art.

FIG. 11 shows a correlation between a count value of large platelets with a volume greater than 10 fL acquired by the implementation and a count value of large platelets with a volume greater than 10 fL acquired by the prior art. In the linear regression analysis of two detection results of the 82 blood samples, the correlation coefficient R2 was 0.940, indicating a good correlation between the method of the present disclosure and the reference method, and the implementation provided by the present disclosure can substantially accurately acquire the count of large platelets with a volume greater than 10 fL.

Figure 12:
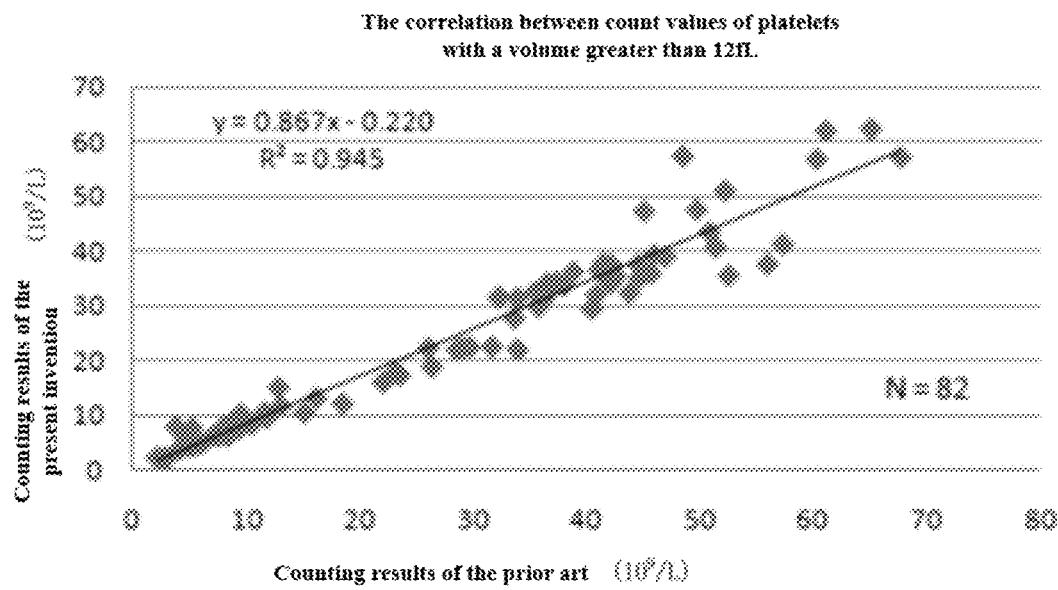
FIG. 12 shows a correlation between a count value of large platelets having a volume greater than 12 fL acquired by the implementation and a count value of large platelets having a volume greater than 12 fL acquired by the prior art.

FIG. 12 shows a correlation between a count value of large platelets with a volume greater than 12 fL acquired by the implementation and a count value of large platelets with a volume greater than 12 fL acquired by the prior art. In the linear regression analysis of two detection results of the 82 blood samples, the correlation coefficient R2 was 0.945, indicating a good correlation between the method of the present disclosure and the reference method, and the implementation provided by the present disclosure can substantially accurately acquire the count of large platelets with a volume greater than 12 fL.

Figure 13:
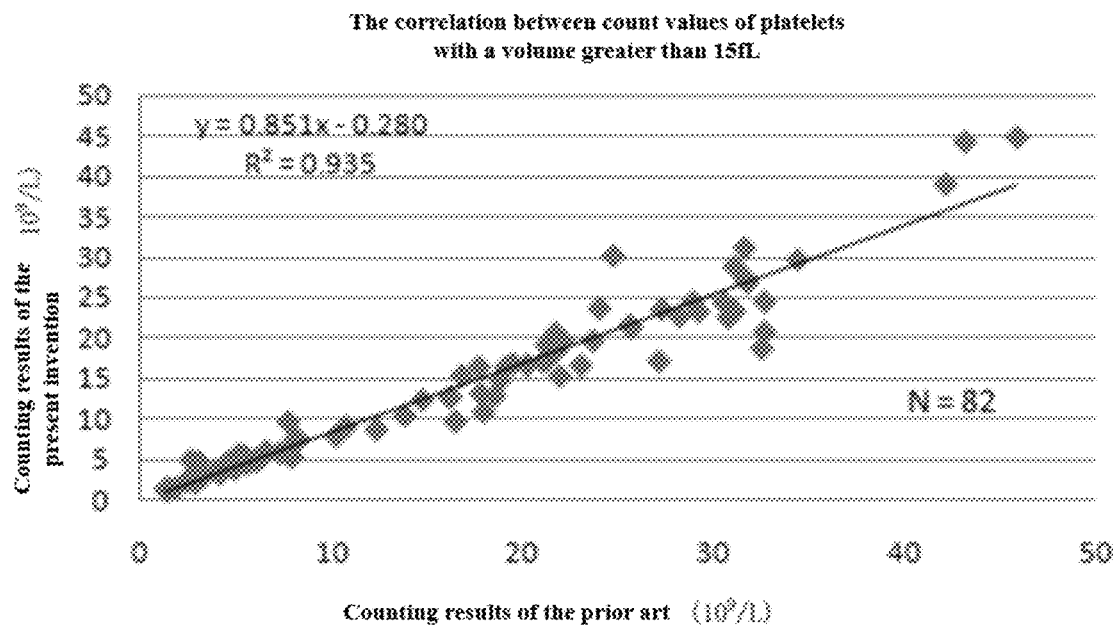
FIG. 13 shows a correlation between a count value of large platelets having a volume greater than 15 fL acquired by the implementation and a count value of large platelets having a volume greater than 15 fL acquired by the prior art.

FIG. 13 shows a correlation between a count value of the large platelets with a volume greater than 15 fL acquired by the implementation and a count value of the large platelets with a volume greater than 15 fL acquired by the prior art. In the linear regression analysis of two detection results of the 82 blood samples, the correlation coefficient R2 was 0.935, indicating a good correlation between the method of the present disclosure and the reference method, and the implementation provided by the present disclosure can substantially accurately acquire the count of large platelets with a volume greater than 15 fL.

Figure 14:
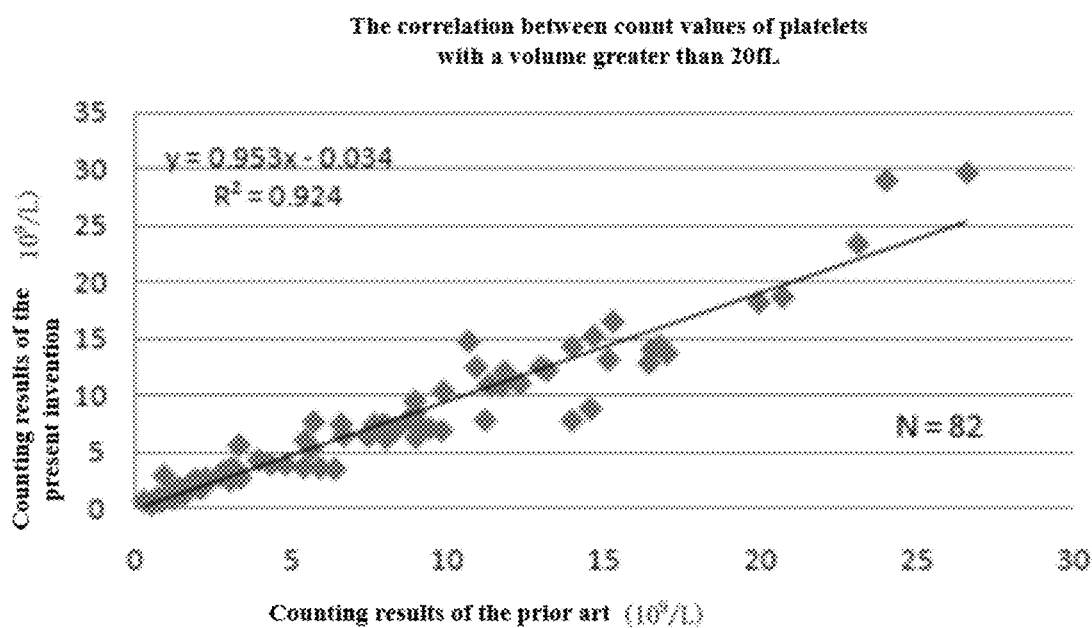
FIG. 14 shows a correlation between a count value of large platelets having a volume greater than 20 fL acquired by the implementation and a count value of large platelets having a volume greater than 20 fL acquired by the prior art.

FIG. 14 shows a correlation between a count value of large platelets with a volume greater than 20 fL acquired by the implementation and a count value of large platelets with a volume greater than 20 fL acquired by the prior art. In the linear regression analysis of two detection results of the 82 blood samples, the correlation coefficient R2 was 0.924, indicating a good correlation between the method of the present disclosure and the reference method, and the implementation provided by the present disclosure can substantially accurately acquire the count of large platelets with a volume greater than 20 fL.

Figure 15:
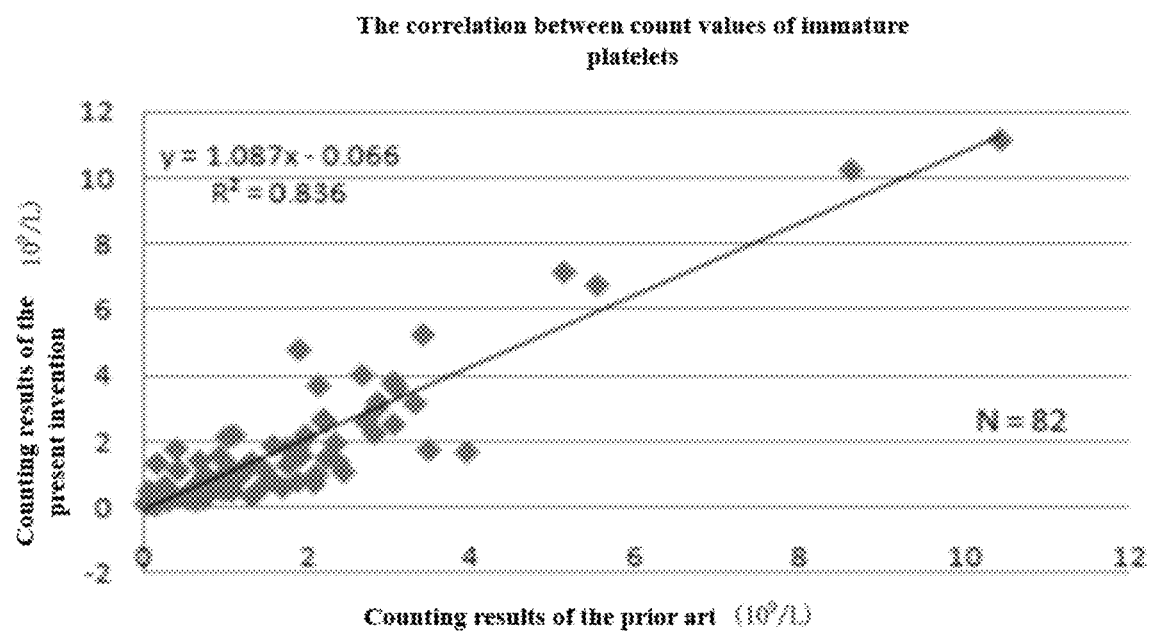
FIG. 15 shows a correlation between a count value of immature platelets acquired by the implementation and a count value of immature platelets acquired by the prior art.

FIG. 15 shows a correlation between a count value of immature platelets acquired by the implementation and a count value of immature platelets acquired by the prior art. In the linear regression analysis of two detection results of the 82 blood samples, the correlation coefficient R2 was 0.836, indicating a good correlation between the method of the present disclosure and the reference method, and the implementation provided by the present disclosure can relatively accurately acquire the count of immature platelets in the blood sample.

A whole blood sample containing nucleated red blood cells was detected using a commercial blood analyzer BC-6800 (SHENZHEN MINDRAY BIO-MEDICAL ELECTRONICS CO., LTD., Shenzhen China), and data acquired from a first and a second test samples was analyzed using any one of the aforementioned implementations.

The BC-6800 blood analyzer comprises a CBC module and a classification module. The CBC module comprises a mixing chamber and a DC impedance detector, wherein the mixing chamber is provided for mixing a aliquot of the blood sample with a diluent agent to prepare a first test sample, and the DC impedance detector is provided for measuring DC impedance signals of the first test sample passing through an aperture in a flow path. The classification module is a classification module for nucleated red blood cells, comprising another mixing chamber, an infrared semiconductor laser and a plurality of optical detectors. The mixing chamber is provided for mixing another aliquot of the blood sample with a hemolytic agent and a fluorescence dye to prepare a second test sample. The infrared semiconductor laser, as a light source with an excitation wavelength of 640 nm, directs its emitted light beam to an orifice of an optical flow chamber. The plurality of the optical detectors can detect forward scattered light signals at an angle of around 1°-10° with respect to the incident light beam, and side scattered light signals and fluorescent signals at an angle of around 65°-115° with respect to the incident light beam, of the second test sample passing through the orifice of the optical flow chamber.

In the CBC module, 4 μL of an anticoagulant whole blood sample was mixed with 1.5 mL of M-68DS diluent (produced by SHENZHEN MINDRAY BIO-MEDICAL ELECTRONICS CO., LTD., Shenzhen China) to prepare a first test sample. In the classification module, 20 μL of the same whole blood sample was mixed with 1 mL of M-68LN Lyse and 20 μL of M-68FN dye (both produced by SHENZHEN MINDRAY BIO-MEDICAL ELECTRONICS CO., LTD., Shenzhen China) for lysing red blood cells and staining blood cells with nucleated acid substance to prepare a second test sample. The M-68LN Lyse was an aqueous solution containing a cationic surfactant and an anionic compound, which was used for lysing red blood cells in blood. The M-68FN dye was an aqueous solution containing a cationic cyanine compound, which was used for staining blood cells with nucleated acid substance in blood.

Figure 16A:
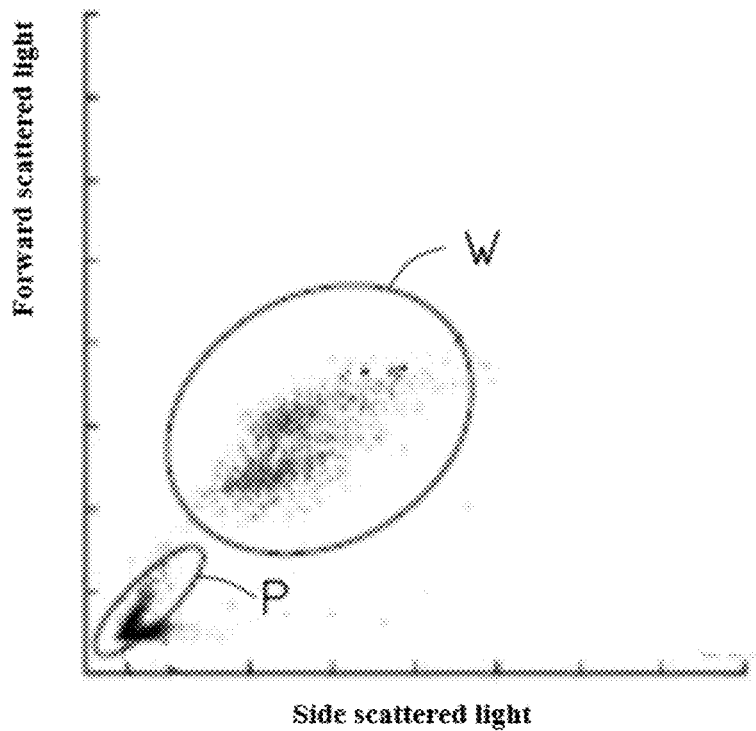
FIG. 16A is a forward scattered light-side scattered light scattergram of a blood sample acquired by an exemplary implementation of the present disclosure.

Based on the forward scattered light signals and the side scattered light signals, a white blood cell region W and a large platelet region P were differentiated in the side scattered light—forward scattered light scattergram shown in FIG. 16A, platelet subpopulation region like large platelet region, and/or immature platelet region was differentiated by the aforementioned methods. Volume distribution data of large platelets and/or immature platelets are acquired by the aforementioned methods. Counting results of large platelets and/or immature platelets may also be acquired.

Figure 16B:
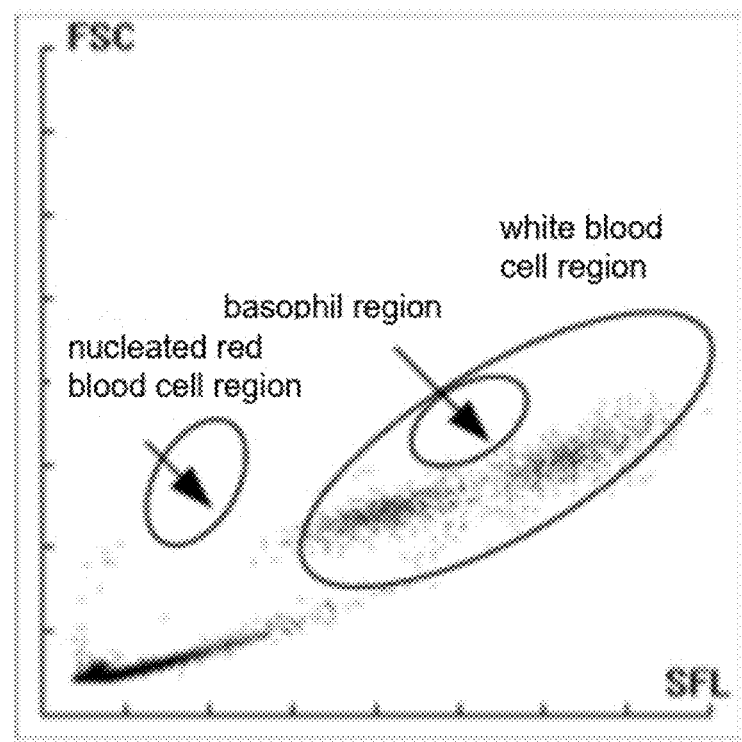
FIG. 16B is an embodiment for differentiating between nucleated red blood cells and white blood cells based on a fluorescent light-forward scattered light scattergram of a blood sample acquired by an exemplary implementation of the present disclosure.

At the same time, as shown in FIG. 16B, based on the forward scattered light-fluorescent light scattergram, other blood cells, including but not limited to white blood cells, nucleated red blood cells, immature cells and blast cells were classified and counted. As shown in FIG. 16B, the method can be used to differentiate among nucleated red blood cells, basophils and white blood cell populations, thereby counting them.

Figure 16C:
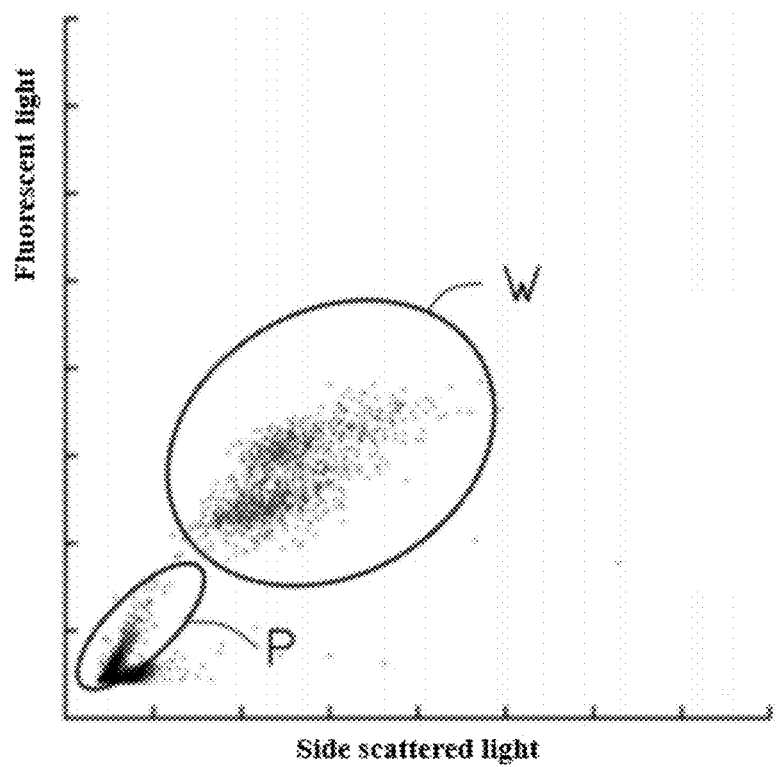
FIG. 16C is a fluorescent light-side scattered light scattergram of a blood sample acquired by an exemplary implementation of the present disclosure.

In the embodiment, based on the side scattered light-fluorescent light scattergram, as shown in FIG. 16C, a white blood cell region W and a large platelet region P can be differentiated. Similarly, volume distribution data and counting results of large platelets and/or immature platelets can be acquired based on the large platelet region. For the specific steps, reference may be made to various implementations and embodiments described above, which will not be repeated herein.

Figure 17:
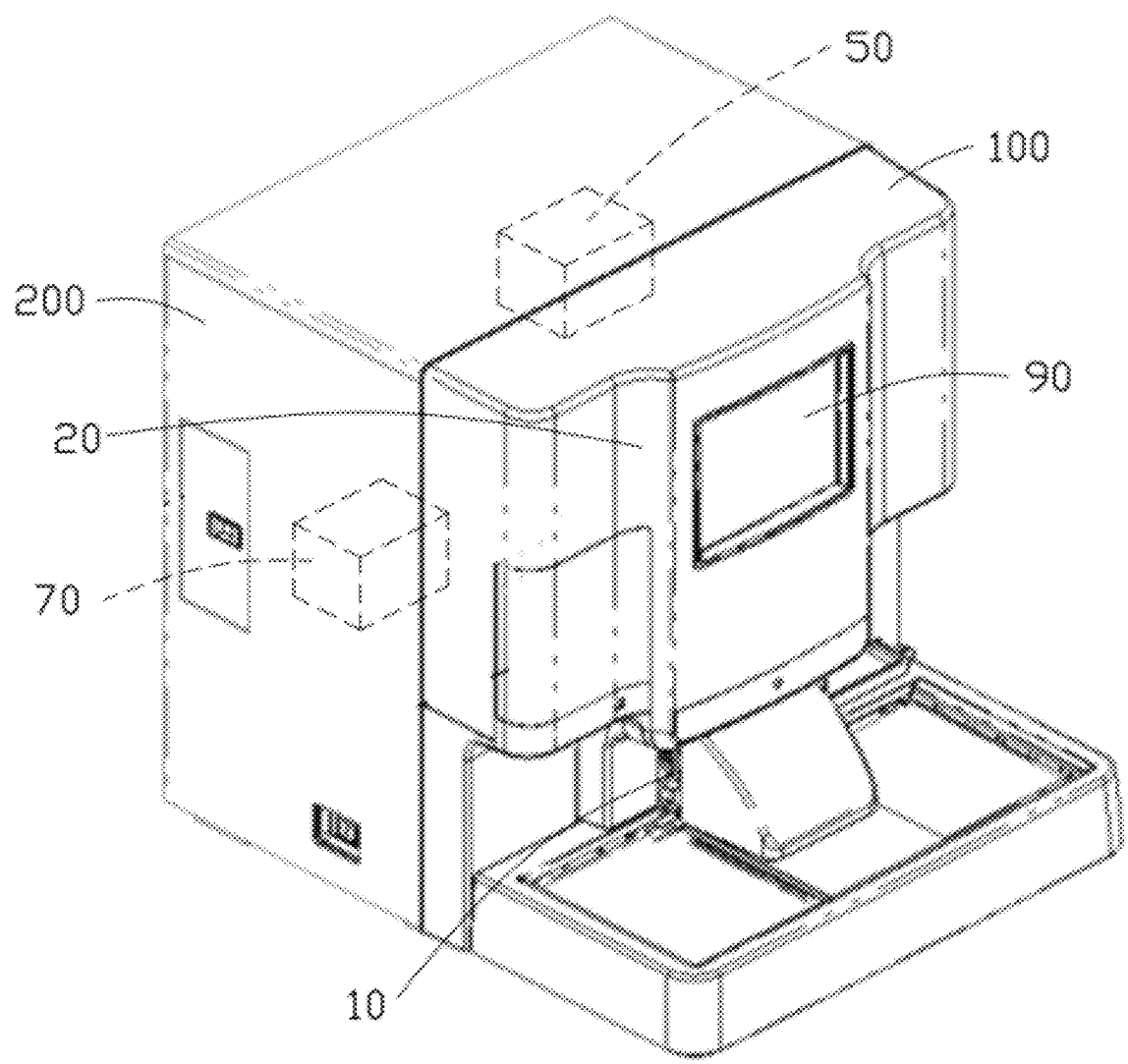
FIG. 17 is an overall stereoscopic diagram of a blood analysis system provided by the present disclosure.

FIG. 17 is an overall stereoscopic diagram of a blood analysis system provided by the present disclosure. As shown in FIG. 17, the blood analysis system comprises a first housing 100, a second housing 200, a sample collection unit 10, a sample treatment device 20, a sample detection device 50, a data analysis module 70 and a user interface 90. In the implementation, the sample detection device 50 and the data analysis module 70 are arranged inside the second housing 200 and are respectively arranged at both sides of the second housing 200. The sample treatment device 20 is arranged inside the first housing 100. The user interface 90 and the sample collection unit 10 are arranged on the outer surface of the first housing 100.

The above implementations are exemplary implementations of the present disclosure, but the present disclosure is not limited by the above examples, and the above exemplary implementations are only for interpreting claims. Any changes or replacements that can be easily conceived by those skilled in the art within the technical scope disclosed in the present disclosure are included within the protection scope of the present disclosure.

What is claimed is:

1. An analysis method of a blood sample, comprising:
    acquiring at least two types of optical signals of a test sample derived from the blood sample in a single test, wherein red blood cells in the test sample are lysed by a lytic agent, blood cells in the test sample are stained by a fluorescence dye, and the at least two types of optical signals comprise forward scattered light signals and fluorescent signals;
    generating a scattergram of the test sample based on the at least two types of optical signals;
    differentiating a white blood cell region from a preset region in the scattergram based on the at least two types of optical signals obtained in the single test;
    acquiring detection data of immature platelets in the test sample prepared by treating the blood sample by the lytic agent and the fluorescence dye based on the preset region; and
    classifying white blood cells in the same test sample into neutrophils, lymphocytes, monocytes and eosinophils, or classifying white blood cells in the same test sample into basophils, based on the at least two types of optical signals of the same test sample that are obtained in the single test,
    wherein both the detection of the immature platelets and the classifying of the white blood cells are acquired from a single test sample, wherein the test sample is treated with a same lytic agent.

2. The analysis method of claim 1, wherein the at least two types of optical signals further comprise side scattered light signals.

3. The analysis method of claim 1, wherein acquiring detection data of immature platelets in the test sample based on the preset region comprises: acquiring volume distribution data of immature platelets in the test sample based on the forward scattered light signals of particles in the preset region.

4. The analysis method of claim 2, wherein acquiring detection data of immature platelets in the test sample based on the preset region comprises: acquiring volume distribution data of immature platelets in the test sample based on the forward scattered light signals and the side scattered light signals of particles in the preset region.

5. The analysis method of claim 1, further comprising:
    determining whether the detection data of immature platelets is abnormal;
    if the detection data of immature platelets is determined to be abnormal, providing an alarm.

6. The analysis method of claim 1, further comprising:
    outputting at least one of: the detection data of immature platelets, the preset region and the scattergram with the preset region being marked.

7. The analysis method of claim 1, further comprising: acquiring a platelet count of the blood sample; calculating a ratio of immature platelets based on the detection data of immature platelets and the platelet count.

8. The analysis method of claim 1, further comprising: acquiring detection data of large platelets in the test sample based on the preset region.

9. A non-volatile computer-readable storage medium with a computer program stored thereon, wherein the computer program implements steps of the analysis method of claim 1 when executed by a processor.

10. A blood analysis system, comprising:
    a sample treatment device comprising at least one mixing chamber for mixing a first aliquot of a blood sample with a lytic reagent to prepare a first test sample, wherein the lytic reagent comprises a hemolytic agent for lysing red blood cells and a fluorescence dye for staining white blood cells;
    a sample detection device comprising an optical detection unit, wherein the optical detection unit comprises an optical flow chamber, a light source and an optical detector, the optical flow chamber is in fluid communication with the mixing chamber, the light source is configured to direct a light beam to the optical flow chamber, the optical detector is configured to detect at least two types of optical signals of the first test sample when each particle of the first test sample is passed through an orifice of the optical flow chamber in a single test, and the at least two types of optical signals comprise forward scattered light signals and fluorescent signals; and
    a data analysis module comprising a signal acquisition module and a classification and counting module;
    wherein the signal acquisition module is configured to acquire the at least two types of optical signals of the first test sample;
    and the classification and counting module is configured to generate a scattergram of the first test sample based on the at least two types of optical signals obtained in the single test, differentiate a white blood cell region from a preset region in the scattergram, and acquire detection data of immature platelets in the first test sample prepared by mixing the blood sample with the hemolytic agent and the fluorescence dye based on the preset region, wherein the classification and counting module is configured to classify white blood cells in the same first test sample into neutrophils, lymphocytes, monocytes and eosinophils or classify white blood cells in the same first test sample into basophils, based on the at least two types of optical signals of the same first test sample that are obtained in the single test, wherein both the detection of the immature platelets and the classifying of the white blood cells are acquired from a single test sample, wherein the test sample is treated with a same lytic agent.

11. The blood analysis system of claim 10, wherein the at least two types of optical signals detected by the optical detector further comprise side scattered light signals.

12. The blood analysis system of claim 10 or 11, wherein the classification and counting module is configured to acquire volume distribution data of immature platelets in the first test sample based on the forward scattered light signals of particles in the preset region.

13. The blood analysis system of claim 11, wherein the classification and counting module is configured to acquire volume distribution data of immature platelets in the first test sample based on the forward scattered light signals and the side scattered light signals of particles in the preset region.

14. The blood analysis system of claim 10, wherein the data analysis module further comprises an alarm module, wherein the alarm module is configured to determine whether the detection data of immature platelets is abnormal, and provide an alarm if the detection data of immature platelets is determined to be abnormal.

15. The blood analysis system of claim 10, further comprising a user interface, wherein the data analysis module is configured to output at least one of the detection data of immature platelets, the preset region and the scattergram with the preset region being marked to the user interface.

16. The blood analysis system of claim 10, wherein the sample treatment device is further configured to mix a second aliquot of the blood sample with a diluent agent to prepare a second test sample;

the sample detection device further comprises an electrical impedance detection unit, wherein the electrical impedance detection unit comprises an aperture and an electrical impedance detector, and the electrical impedance detector is configured to detect electrical impedance signals of the second test sample passing through the aperture;

the signal acquisition module of the data analysis module is configured to acquire the electrical impedance signals of the second test sample;

and the classification and counting module is configured to acquire a platelet count of the blood sample based on the electrical impedance signals, and calculate a ratio of immature platelets based on the detection data of immature platelets and the platelet counts.

17. The blood analysis system of claim 10, wherein the classification and counting module is configured to acquire detection data of large platelets in the first test sample based on the preset region.

* * * * *